United States Patent
Chun et al.

(10) Patent No.: US 10,213,422 B2
(45) Date of Patent: Feb. 26, 2019

(54) COMPOSITIONS AND METHODS OF INHIBITING HISTONE DEACETYLASES

(71) Applicant: YALE UNIVERSITY, New Haven, CT (US)

(72) Inventors: Hyung J. Chun, Guilford, CT (US); Jongmin Kim, Seoul (KR); Cheol Hwangbo, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 15/124,246

(22) PCT Filed: Apr. 13, 2015

(86) PCT No.: PCT/US2015/025552
§ 371 (c)(1),
(2) Date: Sep. 7, 2016

(87) PCT Pub. No.: WO2015/160696
PCT Pub. Date: Oct. 22, 2015

(65) Prior Publication Data
US 2017/0027926 A1    Feb. 2, 2017

Related U.S. Application Data

(60) Provisional application No. 61/979,240, filed on Apr. 14, 2014.

(51) Int. Cl.

| | | |
|---|---|---|
| A61K 31/4704 | (2006.01) | |
| C07D 215/56 | (2006.01) | |
| C07D 215/54 | (2006.01) | |
| C07D 417/14 | (2006.01) | |
| C07D 207/333 | (2006.01) | |
| A61K 31/40 | (2006.01) | |
| A61K 31/427 | (2006.01) | |
| C12Q 1/6883 | (2018.01) | |
| G01N 33/68 | (2006.01) | |

(52) U.S. Cl.
CPC .......... *A61K 31/4704* (2013.01); *A61K 31/40* (2013.01); *A61K 31/427* (2013.01); *C07D 207/333* (2013.01); *C07D 215/54* (2013.01); *C07D 215/56* (2013.01); *C07D 417/14* (2013.01); *C12Q 1/6883* (2013.01); *G01N 33/6893* (2013.01); *C12Q 2600/158* (2013.01); *G01N 2800/321* (2013.01); *G01N 2800/56* (2013.01)

(58) Field of Classification Search
None
See application file for complete search history.

(56) References Cited

U.S. PATENT DOCUMENTS

2009/0076021 A1   3/2009   Plato
2010/0298237 A1   11/2010   Patel et al.

OTHER PUBLICATIONS

Zhao, L et al Circulation 2012 vol. 126 pp. 455-467.*
EMBASE Acc No. 0050943145.*
Isaacs, J. et al., Cancer Res 2013 vol. 73 pp. 1386-1399.*
Silva, A., Mini-Reviews in Medicinal Chemistry, 2005, vol. 5, pp. 893-914.*
International Search Report and Written Opinion for PCT International Application No. PCT/US2015/025552 dated Jul. 9, 2015.
Kim, et al., "Restoration of impaired endothelial myocyte enhancer factor 2 function rescues pulmonary arterial hypertension", Circulation. 131(2), 2014, 190-199.
McKinsey, "Targeting inflammation in heart failure with histone deacetylase inhibitors", Mol Med. 17(5-6), 2011, 434-441.
Nebbioso, et al., "Selective class II HDAC inhibitors impair myogenesis by modulating the stability and activity of HDAC-MEF2 complexes", EMBO Rep. 10(7), 2009, 776-782.
Zhao, et al., "Histone deacetylation inhibition in pulmonary hypertension: therapeutic potential of valproic acid (VPA) and suberoylanilide hydroxamic acid (SAHA)", Circulation. 126(4), 2012, 455-467.

* cited by examiner

*Primary Examiner* — Heidi Reese
(74) *Attorney, Agent, or Firm* — Saul Ewing Arnstein & Lehr LLP; Kathryn Doyle

(57) ABSTRACT

The present invention provides compositions and methods for treating pulmonary hypertension. In one aspect, a method is included for increasing myocyte enhancer factor 2 (MEF2) activity in an endothelial cell comprising exposing the cell to a class IIa histone deacetylase inhibitor. In another aspect, a method is included for treating pulmonary hypertension, such as restoring MEF2 activity, in a subject in need thereof comprising administering to the subject a composition comprising a class IIa histone deacetylase inhibitor. Pharmaceutical compositions for treating pulmonary hypertension in a subject in need thereof and a kit for diagnosing, detecting and/or monitoring pulmonary hypertension are also included.

8 Claims, 46 Drawing Sheets

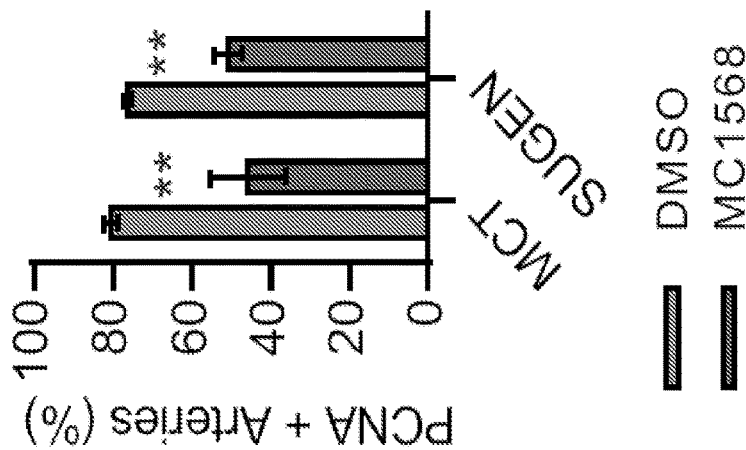
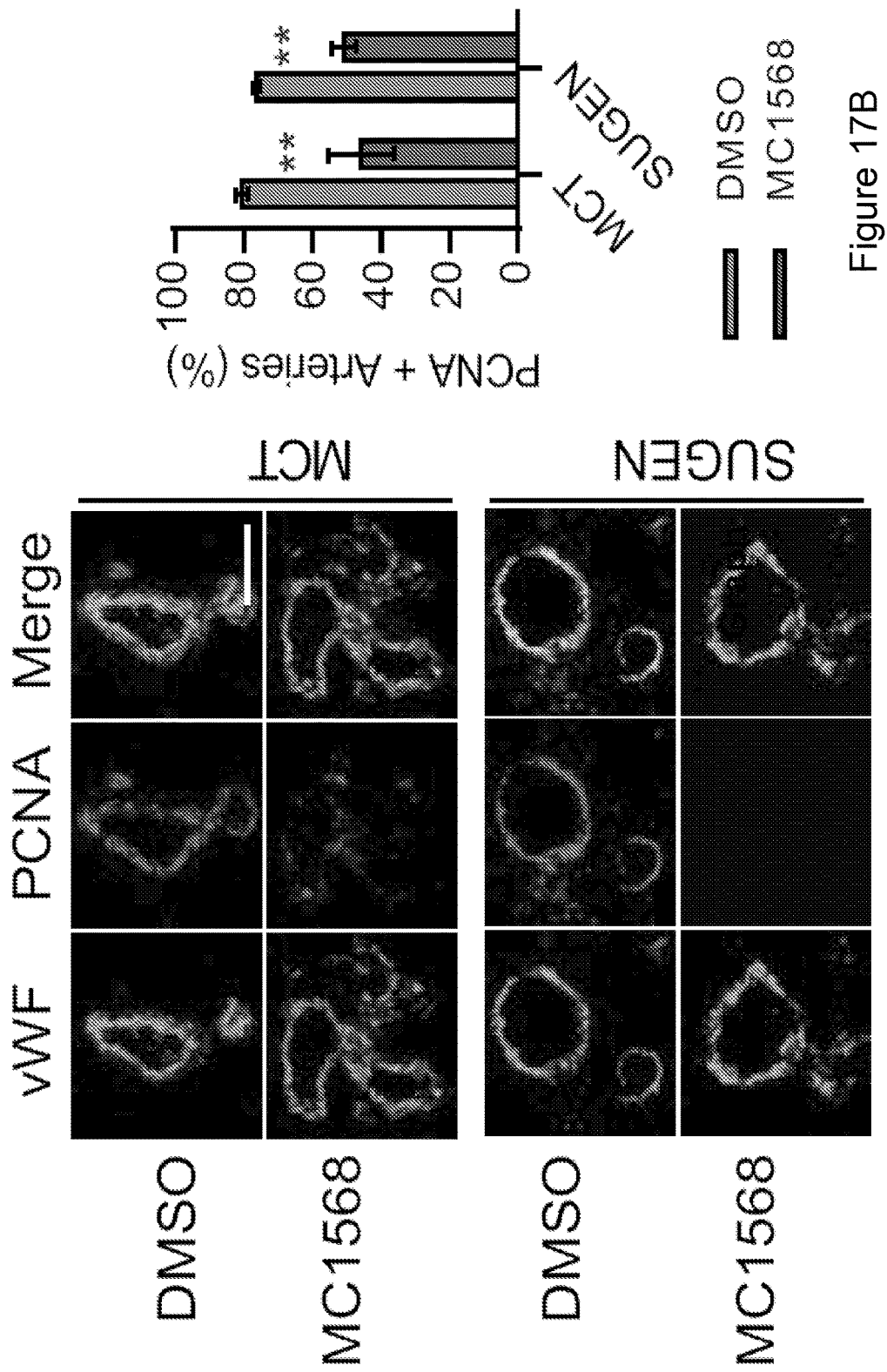
Figure 17A
Figure 17B

*P<0.05

COMPOSITIONS AND METHODS OF INHIBITING HISTONE DEACETYLASES

CROSS-REFERENCE TO RELATED APPLICATIONS

The present application is a 35 U.S.C. § 371 national phase application from, and claims priority to, International Application No. PCT/US2015/025552, filed Apr. 13, 2015, and published under PCT Article 21(2) in English, which claims priority under 35 U.S.C. § 119(e) to U.S. Provisional Application No. 61/979,240, filed Apr. 14, 2014, the entire disclosure of which is incorporated by reference herein as if set forth herein in its entirety all of which applications are incorporated herein by reference in their entireties.

STATEMENT OF RIGHTS TO INVENTIONS MADE UNDER FEDERALLY SPONSORED RESEARCH

This invention was made with government support under HL115008, HL113005, HL095654, and HL060917 awarded by National Institute of Health. The government has certain rights in the invention.

BACKGROUND OF THE INVENTION

Pulmonary arterial hypertension (PAH) is a condition in which the pressure in the lung circulation increases, eventually causing heart failure and death. The etiology of PAH is complex, but aberrant proliferation of the pulmonary artery endothelial cells (PAECs) and pulmonary artery smooth muscle cells (PASMCs) is thought to play an important role in its pathogenesis. Recent identification of a key signaling paradigm in PAECs involving apelin demonstrated the importance of crosstalk among molecules in maintenance of pulmonary vascular homeostasis. The activity of the transcription factor myocyte enhancer factor 2 (MEF2) was also found to be significantly decreased in PAH PAECs. Whether this is the primary event in the development of PAH or part of a downstream cascade remains unknown, but in either case it is an important factor in the progressive vasoconstriction and vascular proliferation that characterize the disease.

Therefore, a need exists for restoring normal function within these cells to reduce or improve pulmonary arterial hypertension.

SUMMARY OF THE INVENTION

The invention includes compositions and methods for treating pulmonary hypertension. In one aspect, the invention includes a method of increasing myocyte enhancer factor 2 (MEF2) activity in an endothelial cell comprising exposing the cell to a class IIa histone deacetylase inhibitor.

In another aspect, the invention includes a method for treating pulmonary hypertension in a subject in need thereof comprising administering to the subject a composition comprising a class IIa histone deacetylase inhibitor.

In yet another aspect, the invention includes a method of restoring MEF2 activity to treat pulmonary hypertension in a subject in need thereof comprising administering to the subject a composition comprising a class IIa histone deacetylase inhibitor.

In still another aspect, the invention includes a pharmaceutical composition for treating pulmonary hypertension comprising at least one class IIa histone deacetylase inhibitor and a pharmaceutically acceptable carrier.

In another aspect, the invention includes a kit for diagnosing, detecting and/or monitoring pulmonary hypertension comprising at least one reagent to measure expression level of one or more transcriptional targets selected from the group consisting of myocyte enhancer factor 2 (MEF2), kriippel like factor 2 (KLF2), connexin 37 (Cx37), connexin 40 (Cx40), fibroblast growth factor 2 (FGF2), and other MEF2 transcriptional targets.

In various embodiments of the above aspects or any other aspect of the invention delineated herein, the inhibitor inhibits at least one of HDAC4, HDAC5 and any combinations thereof. Some examples of inhibitors include, but are not limited to, N-((4-(4-phenylthiazol-2-yl)tetrahydro-2H-pyran-4-yl)methyl)-3-(5-(trifluoromethyl)-1,2,4-oxadiazol-3-yl)benzamide; a quinoline-3-carboxamide compound inhibitor, such as tasquinimod, and a N-hydroxy-but-2-enamide compound inhibitor, such as (aryloxopropenyl)pyrrolyl hydroxylamine, or (E)-3-(5-((E)-3-(3-fluorophenyl)-3-oxoprop-1-en-1-yl)-1-methyl-1H-pyrrol-2-yl)-N-hydroxyacrylamide; a salt, solvate, prodrug or analogue thereof; or any combination thereof.

In various other embodiments of the above aspects or any other aspect of the invention delineated herein, exposing the cell to the inhibitor increases expression of a transcriptional target selected from the group consisting of kriippel like factor 2 (KLF2), connexin 37 (Cx37), connexin 40 (Cx40), and combinations thereof. In another embodiment, the exposure decreases expression of fibroblast growth factor 2 (FGF2). In yet another embodiment, the exposure decreases proliferation of the cell. In still another embodiment, the exposure does not induce a caspase pathway activation in the cell.

In one embodiment, administering the inhibitor increases expression of at least one transcriptional target selected from the group consisting of myocyte enhancer factor 2 (MEF2), kriippel like factor 2 (KLF2), connexin 37 (Cx37), connexin 40 (Cx40), and combinations thereof. In another embodiment, the administration decreases expression of fibroblast growth factor 2 (FGF2). In yet another embodiment, the administration decreases proliferation of pulmonary vascular cells. In still another embodiment, the administration decreases the right ventricular systolic pressure in the subject. In another embodiment, the administration decreases right ventricular hypertrophy. In another embodiment, the administration does not induce a caspase pathway activation in pulmonary vascular cells. In yet another embodiment, the administration does not induce myocardial fibrosis.

BRIEF DESCRIPTION OF THE DRAWINGS

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

FIG. 17A is a panel of images showing PCNA expression in the lungs of the two models receiving either vehicle (DMSO) or MC1568. vWF is shown in in the left column, PCNA is shown in the right column, and merged vWF and PCNA is shown in the right column. Scale bar: 50 µm.

FIG. 17B is a graph showing the percentage of PCNA expression in the lungs of the two models receiving either vehicle (DMSO) or MC1568. **P<0.01 vs. vehicle treated rats in each model.

DETAILED DESCRIPTION OF THE INVENTION

Definitions

Figure 1:
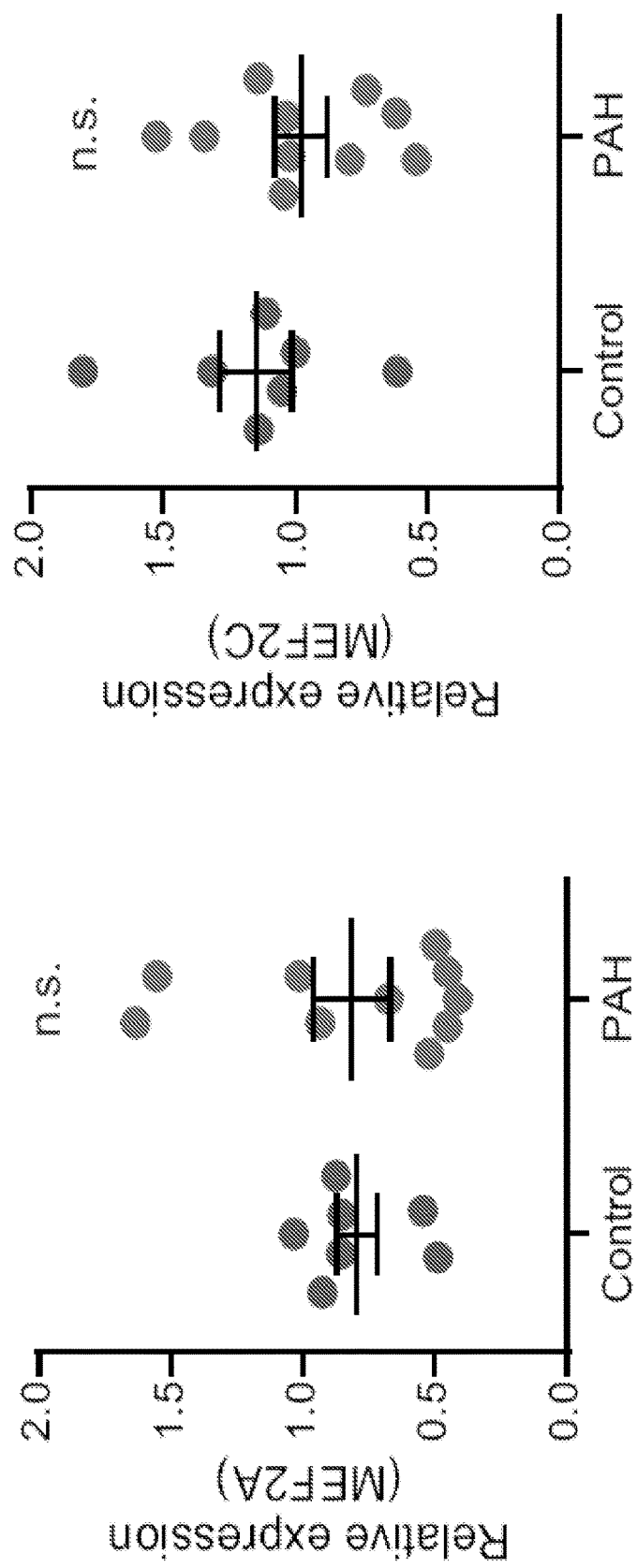
FIG. 1 is a panel of graphs transcript levels of MEF2A and MEF2C in control and pulmonary arterial hypertension (PAH) pulmonary artery endothelial cells (PAECs).

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or within 10%, 9%, 8%, 7%, 6%, 5%, 4%, 3%, 2%, 1%, 0.5%, 0.1%, 0.05%, or 0.01% of the specified value, as such variations are appropriate to perform the disclosed methods. Unless otherwise clear from context, all numerical values provided herein are modified by the term about.

As used herein, the term "analogue" as applied to a compound refers to any enantiomer, diastereoisomer, tautomer, positional isomer, geometric isomer, radioactive derivative, isotopic derivative, homologue, protected or deprotected derivative, or any other analogue of the compound, as contemplated by those skilled in the art.

By "class IIa histone deacetylase" is meant a class of enzymes that removes acetyl groups from a histone. Examples of class IIa histone deacetylases include histone deacetylase 4 (HDAC4), histone deacetylase 5 (HDAC5), histone deacetylase 7 (HDAC7), histone deacetylase 9 (HDAC9), and combinations thereof.

By "N-hydroxy-but-2-enamide compound" or "N-hydroxy-but-2-enamide inhibitor" is meant a compound, or a salt, solvate, prodrug or analogue thereof, comprising Structure I:

Structure I

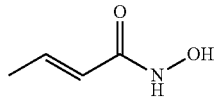

In one embodiment, the N-hydroxy-but-2-enamide compounds includes a molecule such as a (aryloxopropenyl) pyrrolyl hydroxylamine, or a salt, solvate, prodrug or analogue thereof.

By "(aryloxopropenyl)pyrrolyl hydroxylamine" is meant a compound, or a salt, solvate, prodrug or analogue thereof, comprising Structure IIA:

Structure IIA

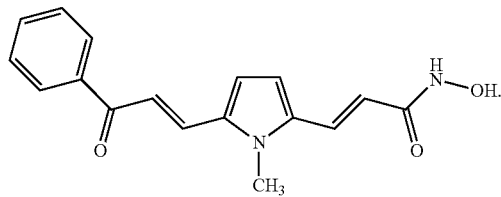

In certain embodiments, "MC1568" or "MC 1568" is an (aryloxopropenyl)pyrrolyl hydroxylamine or (E)-3-(5-((E)-3-(3-fluorophenyl)-3-oxoprop-1-en-1-yl)-1-methyl-1H-pyrrol-2-yl)-N-hydroxyacrylamide, or a salt, solvate, prodrug or analogue thereof, of Structure IIB:

Structure IIB

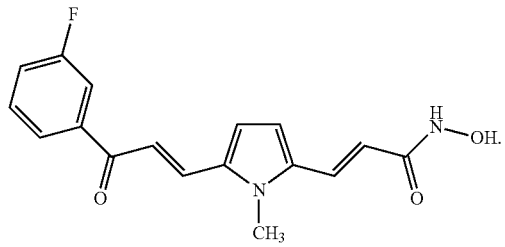

By "pulmonary arterial hypertension" or "pulmonary hypertension" is meant a condition, disorder or disease characterized by abnormally high blood pressure in the arteries of the lungs with a markedly decreased exercise tolerance and increased risk of heart failure. A pressure of greater than 25 mm Hg at rest is abnormally high and is classified as pulmonary hypertension. By "disease" is meant any condition or disorder that damages or interferes with the normal function of a cell, tissue, or organ. Examples of diseases include pulmonary arterial hypertension.

By "quinoline-3-carboxamide compound" or "quinoline-3-carboxamide inhibitor" is meant a compound, or a salt, solvate, prodrug or analogue (such as for example a tautomer) thereof, comprising Structure III:

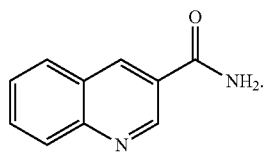

Structure III

In one embodiment, the quinoline-3-carboxamide derivative includes molecules such as tasquinimod or a salt, solvate, prodrug or analogue thereof.

By "tasquinimod" is meant the compound 4-hydroxy-5-methoxy-N,1-dimethyl-2-oxo-N-[4-(trifluoromethyl)phenyl]-1,2-dihydroquinoline-3-carboxamide, or a salt, solvate, prodrug or analogue thereof (Structure IV):

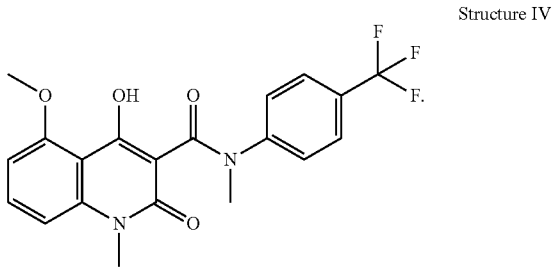 [SMILES: COc1cccc2c1c(O)c(C(=O)N(C)c1ccc(C(F)(F)F)cc1)c(=O)n2C]

Structure IV

As used herein, the term "TMP269" refers to the compound N-((4-(4-phenylthiazol-2-yl)tetrahydro-2H-pyran-4-yl)methyl)-3-(5-(trifluoromethyl)-1,2,4-oxadiazol-3-yl)benzamide (a class IIa HDAC inhibitor), or a salt, solvate, prodrug or analogue thereof (Structure V):

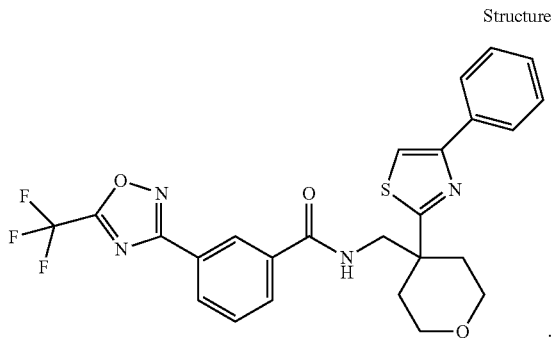

Structure V

By "transcriptional target" is meant any gene that is targeted for an alteration in expression level or activity by a protein or polynucleotide. Examples include, but are not limited to, myocyte enhancer factor 2 (MEF2), kriippel like factor 2 (KLF2), connexin 37 (Cx37), connexin 40 (Cx40), fibroblast growth factor 2 (FGF2), and combinations thereof.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence, or alteration in expression level or relative expression level of a transcriptional target to be detected.

The phrase "differentially present" refers to differences in the quantity and/or the frequency of a transcriptional target present in a sample taken from subjects having a disease as compared to a control subject. A transcriptional target can be differentially present in terms of expression level. A polypeptide or polynucleotide is differentially present between two samples if the amount of the polypeptide or polynucleotide in one sample is statistically significantly different from the amount of the polypeptide or polynucleotide in the other sample, such as a reference. Alternatively or additionally, a polypeptide or polynucleotide is differentially present between two sets of samples if the frequency of detecting the polypeptide or polynucleotide in diseased subjects' samples is statistically significantly higher or lower than in the control samples. A transcriptional target is present in one sample at an expression level, but at a different expression level in another sample is differentially present.

By "effective amount" is meant the amount required to reduce or improve at least one symptom of a disease relative to an untreated patient. The effective amount of active compound(s) used to practice the present invention for therapeutic treatment of a disease varies depending upon the manner of administration, the age, body weight, and general health of the subject.

The term "expression" as used herein is defined as the transcription and/or translation of a particular nucleotide sequence driven by its promoter.

By "fragment" is meant a portion of a polynucleotide or nucleic acid molecule. This portion contains, preferably, at least 10%, 20%, 30%, 40%, 50%, 60%, 70%, 80%, or 90% of the entire length of the reference nucleic acids. A fragment may contain 10, 20, 30, 40, 50, 60, 70, 80, 90, or 100, 200, 300, 400, 500, 600, 700, 800, 900, 1000, 1500, 2000 or 2500 (and any integer value in between) nucleotides. The fragment, as applied to a nucleic acid molecule, refers to a subsequence of a larger nucleic acid. A "fragment" of a nucleic acid molecule may be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

As used herein, the term "inhibit" is meant to refer to a decrease in biological state. For example, the term "inhibit" may be construed to refer to the ability to negatively regulate the expression, stability or activity of a protein, including but not limited to transcription of a protein mRNA, stability of a protein mRNA, translation of a protein mRNA, stability of a protein polypeptide, a protein post-translational modifications, a protein activity, a protein signaling pathway or any combination thereof.

By "inhibitor" is meant a compound or molecule that prevents or decreases an enzyme's activity. For example, a class IIa histone deacetylase inhibitor is a compound or molecule that prevents or decreases one or more class IIa histone deacetylases' activity.

"Instructional material," as that term is used herein, includes a publication, a recording, a diagram, or any other medium of expression that may be used to communicate the usefulness of the compounds of the invention. In some instances, the instructional material may be part of a kit useful for effecting alleviating or treating the various diseases or disorders recited herein. Optionally, or alternately, the instructional material may describe one or more methods of alleviating the diseases or disorders in a cell or a tissue of a mammal. The instructional material of the kit may, for example, be affixed to a container that contains the compounds of the invention or be shipped together with a container that contains the compounds. Alternatively, the instructional material may be shipped separately from the container with the intention that the recipient uses the instructional material and the compound cooperatively. For example, the instructional material is for use of a kit; instructions for use of the compound; or instructions for use of a formulation of the compound.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutical composition" or "pharmaceutically acceptable composition" refers to a mixture of at least one compound or molecule useful within the invention with a pharmaceutically acceptable carrier. The pharmaceutical composition facilitates administration of the compound or molecule to a patient. Multiple techniques of administering a compound or molecule exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or molecule useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound or molecule useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which may be hydrolyzed into the monomeric "nucleotides." The monomeric nucleotides may be hydrolyzed into nucleosides. As used herein polynucleotides include, but are not limited to, all nucleic acid sequences that are obtained by any means available in the art, including, without limitation, recombinant means, i.e., the cloning of nucleic acid sequences from a recombinant library or a cell genome, using ordinary cloning technology and PCR™, and the like, and by synthetic means. The following abbreviations for the commonly occurring nucleic acid bases are used. "A" refers to adenosine, "C" refers to cytosine, "G" refers to guanosine, "T" refers to thymidine, and "U" refers to uridine. The term "RNA" as used herein is defined as ribonucleic acid. The term "recombinant DNA" as used herein is defined as DNA produced by joining pieces of DNA from different sources.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

As used herein, the terms "prevent," "preventing," "prevention," and the like refer to reducing the probability of developing a disorder or condition in a subject, who does not have, but is at risk of or susceptible to developing a disorder or condition.

By "reduces" or "decreases" is meant a negative alteration of at least 10%, 25%, 50%, 75%, or 100%.

By "reference" is meant a standard or control. A "reference" is also a defined standard or control used as a basis for comparison.

As used herein, "sample" or "biological sample" refers to anything, which may contain the transcriptional target (e.g., polypeptide, polynucleotide, or fragment thereof) for which a transcriptional target assay is desired. The sample may be a biological sample, such as a biological fluid or a biological tissue. In one embodiment, a biological sample is a tissue sample including pulmonary vascular cells. Such a sample may include diverse cells, proteins, and genetic material. Examples of biological tissues also include organs, tumors, lymph nodes, arteries and individual cell(s). Examples of biological fluids include urine, blood, plasma, serum, saliva, semen, stool, sputum, cerebral spinal fluid, tears, mucus, amniotic fluid or the like.

As used herein, the term "sensitivity" is the expression level of the transcriptional target-detected in subjects with a particular disease.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

A "subject" or "patient," as used therein, may be a human or non-human mammal. Non-human mammals include, for example, livestock and pets, such as ovine, bovine, porcine, canine, feline and murine mammals. Preferably, the subject is human.

As used herein, the terms "treat," treating," "treatment," and the like refer to reducing or improving a disorder and/or symptom associated therewith. It will be appreciated that, although not precluded, treating a disorder or condition does not require that the disorder, condition or symptoms associated therewith be completely ameliorated or eliminated.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Pulmonary Arterial Hypertension (PAH)

Pulmonary arterial hypertension (PAH) is a vascular disease of the pulmonary vasculature that primarily targets the small pulmonary arteries. The hallmark of terminal PAH is aberrant proliferation of both the pulmonary artery endothelial cells and pulmonary artery smooth muscle cells (PAECs and PASMCs), pulmonary vascular cells, ultimately culminating in the formation of lumen obliterating plexiform lesions. Research into the molecular events originating in pulmonary endothelial cells that contribute to the PAH have found that levels of apelin and fibroblast growth factor 2 (FGF2) are increased and myocyte enhancer factor 2 (MEF2) is decreased in PAH pulmonary endothelial cells.

Compositions

The present invention includes compositions that are useful for treating pulmonary arterial hypertension or symptoms thereof by reducing proliferation of pulmonary vascular cells. Thus, one embodiment includes a composition comprising an inhibitor of a class IIa histone deactylase.

In another aspect, the invention includes a pharmaceutical composition for treating pulmonary hypertension in a subject in need thereof comprising at least one class IIa histone deacetylase inhibitor and a pharmaceutically acceptable carrier. The class IIa histone deacetylase inhibitor includes molecules that inhibit any one of histone deacetylase 4 (HDAC4), histone deacetylase 5 (HDAC5), histone deacetylase 7 (HDAC7), histone deacetylase 9 (HDAC9), and combinations thereof. In an exemplary embodiment, the class IIa histone deacetylase inhibitor inhibits at least one of HDAC4, HDAC5 and combinations thereof.

Examples of class IIa histone deacetylase inhibitors include a N-hydroxy-but-2-enamide compound. An N-hydroxy-but-2-enamide compound comprises Structure I, or a salt, solvate, prodrug or analogue thereof:

Structure I

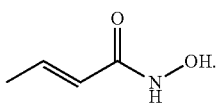

In one embodiment, the N-hydroxy-but-2-enamide compound includes molecules such as an (aryloxopropenyl) pyrrolyl hydroxylamine compound. In certain embodiments, the (aryloxopropenyl)pyrrolyl hydroxylamine is MC1568 or (E)-3-(5-((E)-3-(3-fluorophenyl)-3-oxoprop-1-en-1-yl)-1- methyl-1H-pyrrol-2-yl)-N-hydroxyacrylamide, or a salt, solvate, prodrug or analogue thereof, of Structure IIB, or a salt, solvate, prodrug or analogue thereof:

Structure IIB

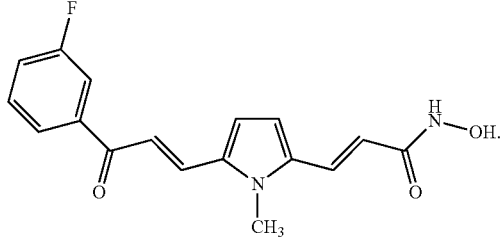

In one embodiment, the invention includes the class IIa histone deacetylase inhibitor is a compound having the formula of Structure I, or a salt, solvate, prodrug or analogue thereof. In another embodiment, the class IIa histone deacetylase inhibitor is a compound having the formula of Structure IIA or IIB, or a salt, solvate, prodrug or analogue thereof.

In another exemplary embodiment, the class IIa histone deacetylase inhibitor includes a quinoline-3-carboxamide derivative. A quinoline-3-carboxamide compound comprises Structure III:

Structure III

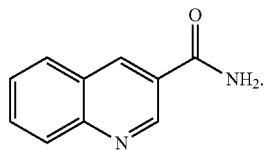

In one embodiment, the quinoline-3-carboxamide compound comprises tasquinimod, or a salt, solvate, prodrug, or analogue thereof. In an exemplary embodiment, the quinoline-3-carboxamide compound is the compound of Structure IV, or a salt, solvate, prodrug or analogue thereof.

Structure IV

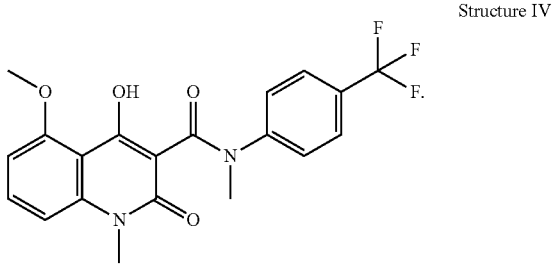 [SMILES: COc1cccc2c1c(O)c(C(=O)N(C)c1ccc(C(F)(F)F)cc1)c(=O)n2C]

In another exemplary embodiment, the class IIa histone deacetylase inhibitor includes TMP269 or N-((4-(4-phenylthiazol-2-yl)tetrahydro-2H-pyran-4-yl)methyl)-3-(5-(trifluoromethyl)-1,2,4-oxadiazol-3-yl)benzamide and derivatives thereof. TMP269 is a compound of Structure V:

Structure V

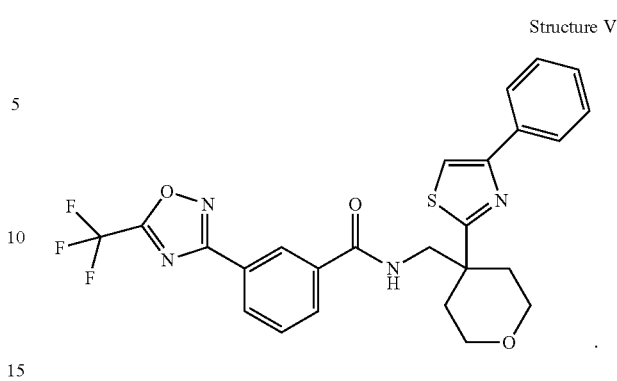

In one embodiment, the inhibitor is selected from the group consisting of a N-hydroxy-but-2-enamide compound, a quinoline-3-carboxamide compound, N-((4-(4-phenylthiazol-2-yl)tetrahydro-2H-pyran-4-yl)methyl)-3-(5-(trifluoromethyl)-1,2,4-oxadiazol-3-yl)benzamide, a salt, solvate, prodrug, analogue and any combinations thereof.

Methods

The present invention includes methods of treating pulmonary hypertension in a subject in need thereof comprising exposing the cell to a class IIa histone deacetylase inhibitor. Myocyte enhancer factor 2 (MEF2) activity is found to be decreased in pulmonary artery endothelial cells of subjects with pulmonary arterial hypertension (PAH). By selectively inhibiting class IIa histone deacetylases (HDACs) restoration of MEF2 transcriptional targets decreased pulmonary artery endothelial cell migration and proliferation, and ameliorated experimental pulmonary hypertension (PH) models.

Thus in one aspect, the invention includes a method of increasing myocyte enhancer factor 2 (MEF2) activity in a cell, such as an endothelial or non-endothelial cell, comprising exposing the cell to a class IIa histone deacetylase inhibitor. The exposure of the cell to the class IIa histone deacetylase inhibitor increases expression of a transcriptional target selected from the group consisting of krüppel like factor 2 (KLF2), connexin 37 (Cx37), connexin 40 (Cx40), and combinations thereof. In another embodiment, the exposure decreases expression of fibroblast growth factor 2 (FGF2). In yet another embodiment, the exposure decreases proliferation of the cell and/or does not induce a caspase pathway activation in the cell.

In another aspect, the invention includes a method of restoring MEF2 activity to treat pulmonary hypertension in a subject in need thereof comprising administering to the subject a composition comprising a class IIa histone deacetylase inhibitor. In one embodiment, the administration increases expression of at least one transcriptional target selected from the group consisting of myocyte enhancer factor 2 (MEF2), krüppel like factor 2 (KLF2), connexin 37 (Cx37), connexin 40 (Cx40), and combinations thereof. In another embodiment, the administration decreases expression of fibroblast growth factor 2 (FGF2).

The method further treats pulmonary hypertension by decreasing ventricular systolic pressure and/or decreasing proliferation of pulmonary vascular cells in the subject. The administration also does not induce a caspase pathway activation in pulmonary vascular cells and/or does not induce myocardial fibrosis in the subject.

The methods herein include a method of identifying a subject in need of therapeutic intervention to reduce or improve a symptom of pulmonary arterial hypertension, a method of reducing proliferation of pulmonary vascular cells in a subject in need thereof, and a method of treating pulmonary arterial hypertension in a subject in need thereof. Identifying a subject in need of such treatment can be in the judgment of a subject or a health care professional and can be subjective (e.g. opinion) or objective (e.g. measurable by a test or diagnostic method). Identification of those subjects "at risk" can be made by any objective or subjective determination by a diagnostic test or opinion of a subject or health care provider (e.g., genetic test, enzyme or protein marker, Marker (as defined herein), family history, and the like). In particular, detecting an alteration in the level of a transcriptional target can aid in the identification of subject in need of therapeutic intervention to prevent or treat pulmonary arterial hypertension.

The therapeutic methods (which include prophylactic treatment) to reduce proliferation of pulmonary vascular cells or to treat pulmonary arterial hypertension in a subject include administration of a therapeutically effective amount of a class IIa histone deacetylase inhibitor to a subject (e.g., animal, human) in need thereof, including a mammal, particularly a human. Such treatment will be suitably administered to subjects, particularly humans, suffering from, having, susceptible to, or at risk for pulmonary arterial hypertension or a symptom thereof.

Kits

In one aspect, kits for diagnosing, detecting and/or monitoring PAH, wherein the kits can be used to detect the expression levels of transcription targets aberrantly expressed in pulmonary arterial hypertension described herein. For example, the kits can be used to detect any one or more of the transcriptional targets potentially differentially present in samples of test subjects vs. normal subjects (e.g., myocyte enhancer factor 2 (MEF2), kriippel like factor 2 (KLF2), connexin 37 (Cx37), connexin 40 (Cx40), and fibroblast growth factor 2 (FGF2) transcripts) or control transcripts. If desired a kit includes any one or more of the following: reagents to measure expression levels of one or more transcriptional targets selected from the group consisting of myocyte enhancer factor 2 (MEF2), kriippel like factor 2 (KLF2), connexin 37 (Cx37), connexin 40 (Cx40), fibroblast growth factor 2 (FGF2), and other MEF2 transcriptional targets. The kits have many used in the context of the present invention. For example, the kits can be used to differentiate if a subject has PAH, or has a propensity to develop PAH, thus aiding PAH diagnosis. The kits can also be used to identify agents that modulate expression of one or more of the herein-described biomarkers in in vitro or in vivo animal models for PAH.

Pharmaceutical Compositions and Formulations

The invention also encompasses the use of a pharmaceutical composition of the invention to practice the methods of the invention. In one aspect, the invention includes a pharmaceutical composition for treating pulmonary hypertension in a subject in need thereof comprising at least one class IIa histone deacetylase inhibitor and a pharmaceutically acceptable carrier. Such a pharmaceutical composition may be provided in a form suitable for administration to a subject, and may be comprise one or more pharmaceutically acceptable carriers, one or more additional ingredients, or some combination of these. The at least one composition of the invention may comprise a physiologically acceptable salt, such as a compound contemplated within the invention in combination with a physiologically acceptable cation or anion, as is well known in the art.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In one embodiment, the compositions of the invention are formulated using one or more pharmaceutically acceptable excipients or carriers. In one embodiment, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

Administration/Dosing

In the clinical settings, delivery systems for the therapeutic composition can be introduced into a patient by any of a number of methods, each of which is familiar in the art. For instance, a pharmaceutical composition can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen, et al. PNAS 91: 3054-3057 (1994)).

In one exemplary implementation, the pharmaceutical composition is directly injected into pulmonary arterial tissue. U.S. Ser. No. 10/914,829 describes a protocol for direct injection. Direct injection or application of a viral vector into pulmonary arterial tissue can restrict expression of the miRNAs to pulmonary arterial tissue (Gutzman et al, Circ. Res. (1993); French et al., Circulation. (1994)). The preparation may also be provided to cells ex vivo. Cells containing the class IIa histone deacetylase inhibitors are then administered to the patient.

The regimen of administration may affect what constitutes an effective amount. The therapeutic formulations may be administered to the patient either prior to or after the manifestation of symptoms associated with the disease or condition. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or condition in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

Routes of Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The Results of the experiments disclosed herein are now described.

Example 1: Restoration of MEF2 Function Via Selective Inhibition of Class IIa Histone Deacetylase Inhibition Pulmonary arterial hypertension (PAH) is a progressive disease of the pulmonary arterioles, characterized by increased pulmonary arterial pressure and right ventricular failure. The etiology of PAH is complex, but aberrant proliferation of the pulmonary artery endothelial cells (PAECs) and pulmonary artery smooth muscle cells (PASMCs) is thought to play an important role in its pathogenesis. Recent identification of a key signaling paradigm in PAECs involving apelin demonstrated the importance of crosstalk among these molecules in maintenance of pulmonary vascular homeostasis. The transcription factor myocyte enhancer factor 2 (MEF2) was significantly decreased in PAH PAECs. This is found herein to be mediated by increased nuclear localization of two class IIa histone deacetylases (HDACs) in PAH PAECs, namely HDAC4 and HDAC5, which negatively regulate MEF2 function. Selective inhibition of class IIa HDACs led to restoration of MEF2 transcriptional targets, decreased PAH PAEC migration and proliferation, and amelioration of experimental pulmonary hypertension (PH) models. These studies demonstrate that restoration of endothelial MEF2 activity, achieved by selective inhibition of class IIa HDACs, is a promising therapeutic strategy in PAH.

Figure 2:
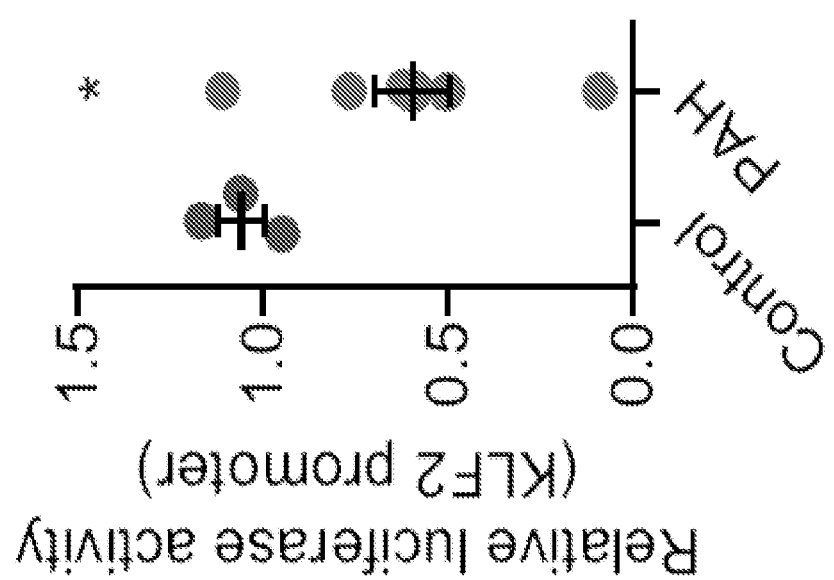
FIG. 2 is a graph showing the relative luciferase activity by luciferase reporters driven by KLF2 promoter region using control and PAH PAECs were lower.
Figure 3:
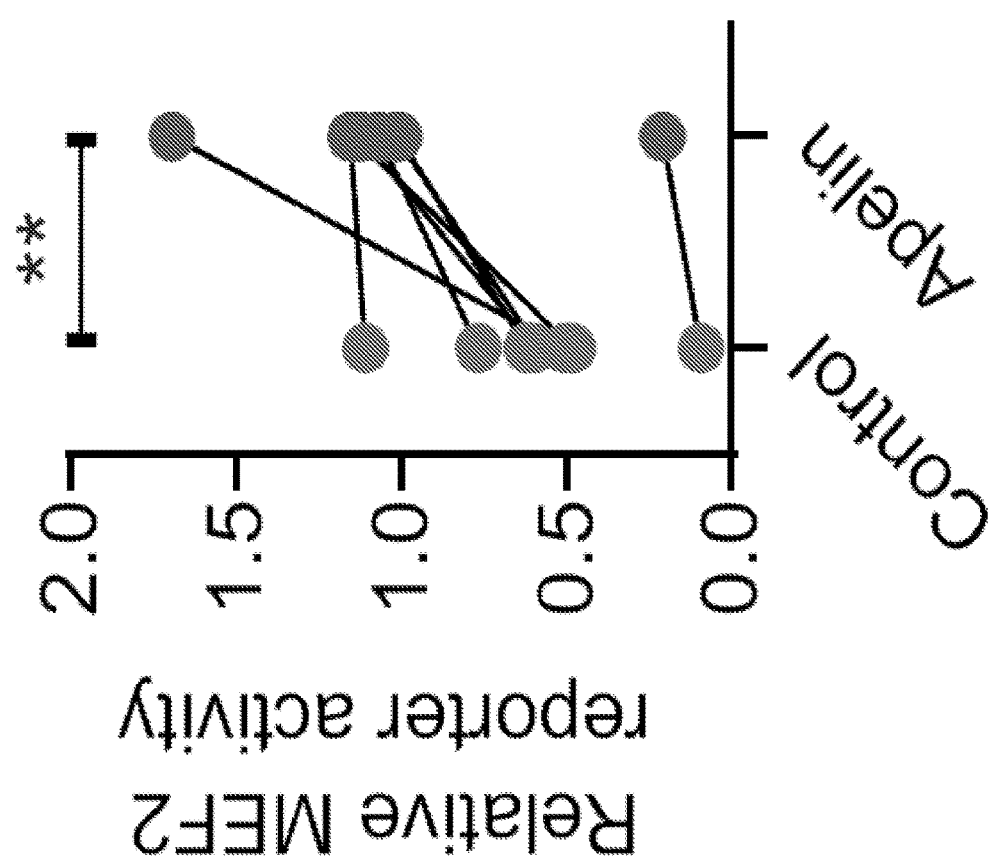
FIG. 3 is a graph showing results from the MEF2 reporter assay in PAH PAECs to determine the response to apelin stimulation (1 µM for 24 h). **P<0.01 vs. control.

To further corroborate these findings to the PAH context, MEF2 activity was evaluated whether it was impaired in PAH PAECs. Transcript levels of MEF2A and MEF2C were not significantly different between control and PAH PAECs (FIG. 1). MEF2 responsive reporter from the Krüppel Like Factor 2 (KLF2) promoter was significantly lower in PAH PAECs compared to controls (FIG. 2). Moreover, stimulation of PAH PAECs with apelin led to a significant augmentation of the MEF2 reporter activity in PAH PAECs tested, demonstrating that MEF2 activity can be augmented by restoring apelin signaling (FIG. 3).

Figure 4A:
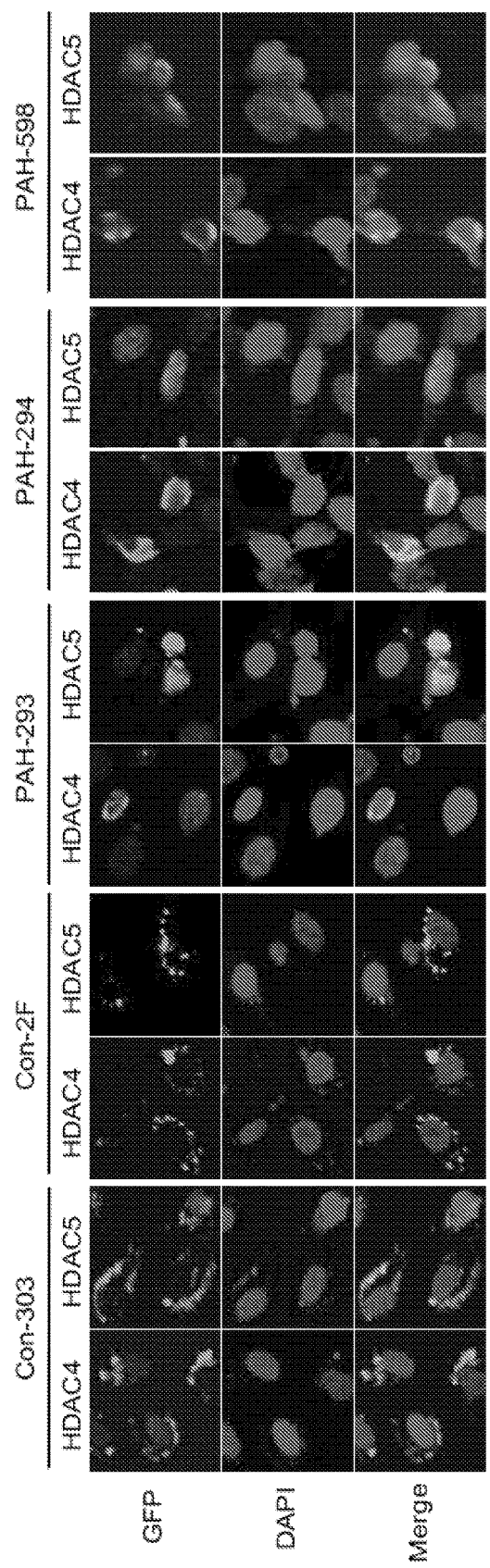
FIG. 4A is a panel of images showing intracellular localization of either transfected GFP tagged HDAC4 or HDAC5 in control and PAH PAECs. GFP is shown in the upper images, DAPI nuclear stain is shown in the middle images and merged GFP and DAPI is shown in the lower images.
Figure 4B:
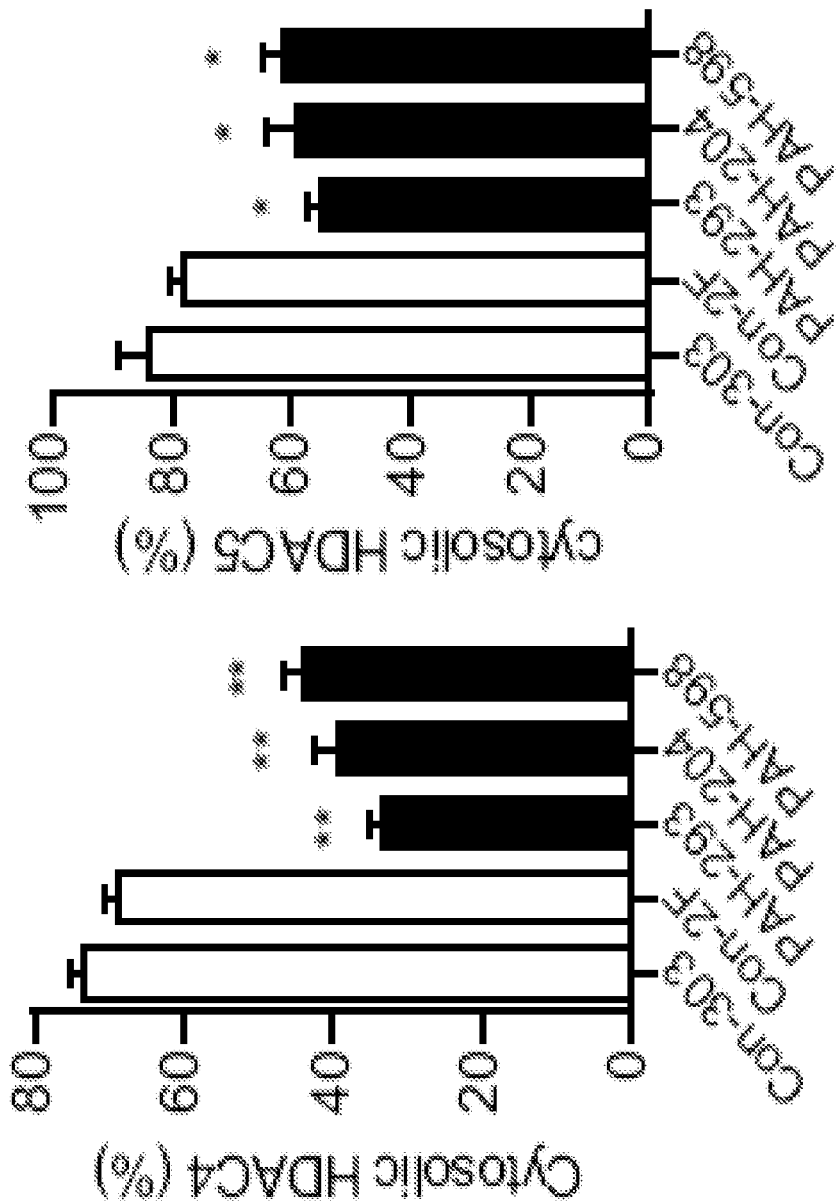
FIG. 4B is a panel of graphs showing the percentage of cytosolic HDAC4 (left graph) and HDAC5 (right graph). **P<0.01 vs. Con-303, *P<0.05 vs. Con-303.
Figure 5A:
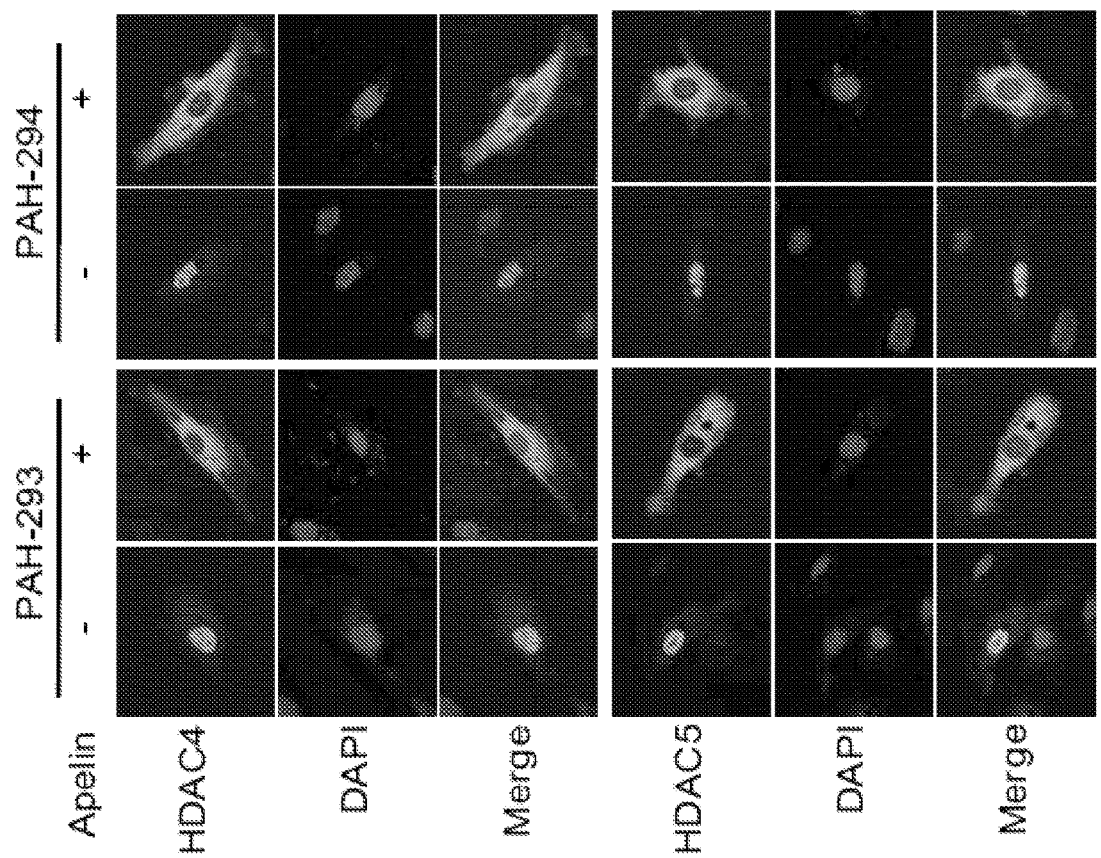
FIG. 5A is a panel of images showing HDAC4-GFP or HDAC5-GFP intracellular localization in response to apelin (1 µM for 1 h) stimulation in PAH PAECs.
Figure 5B:
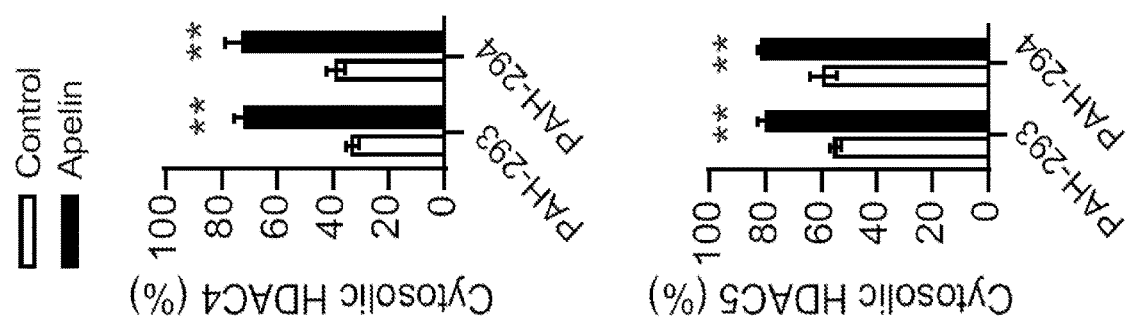
FIG. 5B is a panel of graphs showing the percentage of cytosolic HDAC4 (upper graph) and HDAC5 (lower graph). **P<0.01 vs. control.
Figures 6A, 6B:
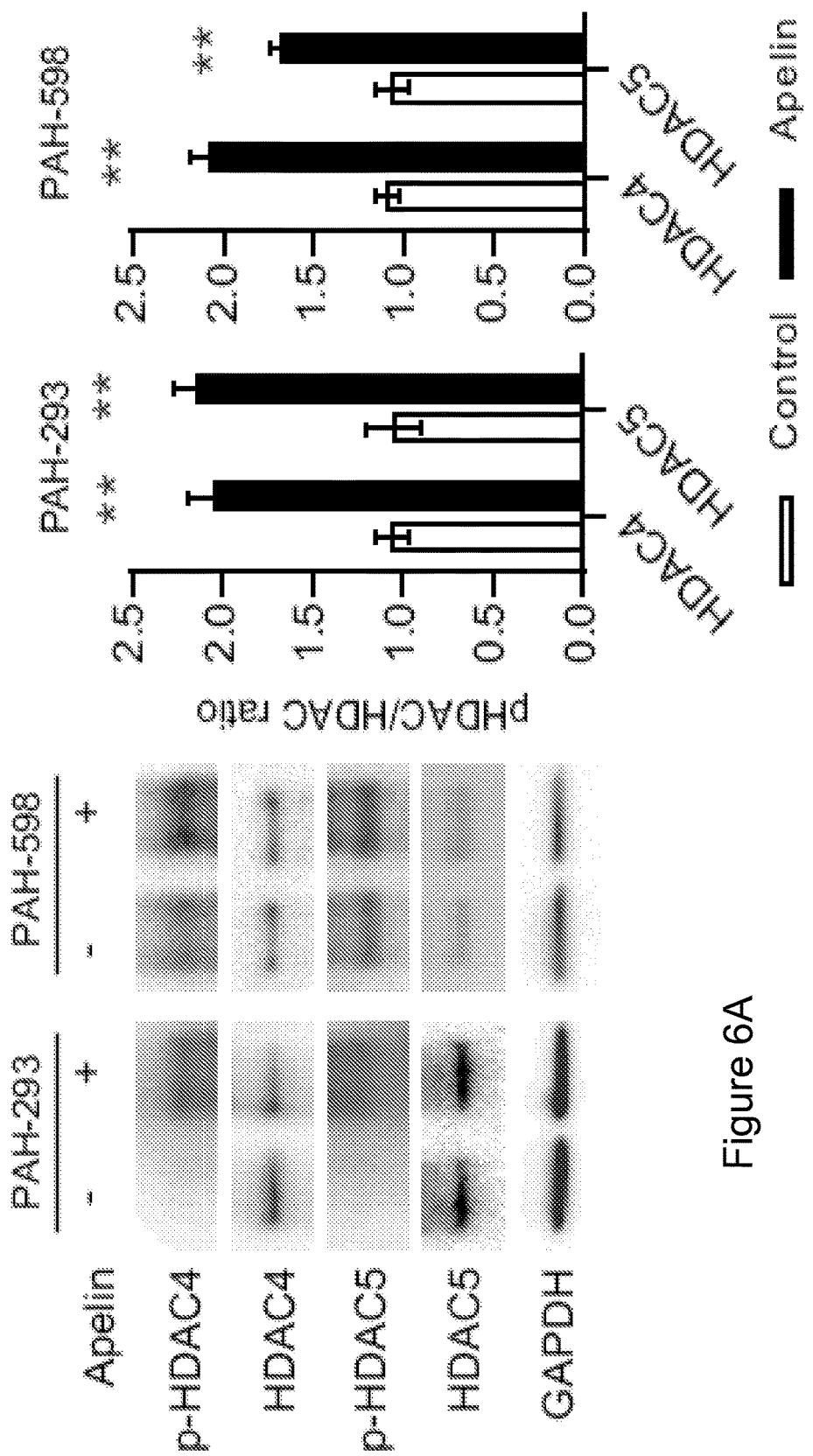
FIG. 6A is a panel of blots showing phosphorylation of endogenously expressed HDAC4 and HDAC5 in response to apelin (1 µM for 1 h) stimulation in PAH PAECs.
FIG. 6B is a panel of graphs showing phosphorylation of endogenously expressed HDAC4 and HDAC5 in response to apelin (1 µM for 1 h) stimulation in PAH PAECs. **P<0.01 vs. unstimulated controls.

MEF2 is known to be regulated by multiple mechanisms, one of which is its inhibition by class IIa histone deacetylases (HDACs). Interestingly, recent studies suggested that broad spectrum histone deacetylase (HDAC) inhibitors can ameliorate hypoxia mediated pulmonary vascular remodeling in rats, but these studies were limited by: 1) inadequate definition of specific cell types or signaling mechanisms that are targeted by the HDAC inhibitors to protect against pulmonary vascular remodeling; 2) use of chronic hypoxia-based PH model that lacks robust pulmonary vascular remodeling; and 3) lack of identification of specific HDAC binding partners that mediate their therapeutic effects in the pulmonary vasculature. Moreover, concern regarding the use of broad spectrum HDAC inhibitors was raised by a separate study demonstrating that certain HDAC inhibitors can worsen right ventricular (RV) function and induce RV capillary death, which could be detrimental in clinical PAH. To address these limitations, a series of studies to evaluate the potential role of specifically targeting class IIa HDACs (to which HDAC4 and HDAC5 belong) in PAH was carried out. PAH PAECs had a significantly higher fraction of transfected HDAC4-GFP and HDAC5-GFP localized to the nucleus, compared to control PAECs (FIGS. 4A and 4B). Moreover, stimulation of PAH PAECs with apelin led to robust cytoplasmic translocation of both HDAC4-GFP and HDAC5-GFP (FIGS. 5A and 5B), as well as marked increase in phosphorylation of HDAC4 and HDAC5 (FIGS. 6A and 6B), which is closely associated with their cytoplasmic translocation.

Figure 7:
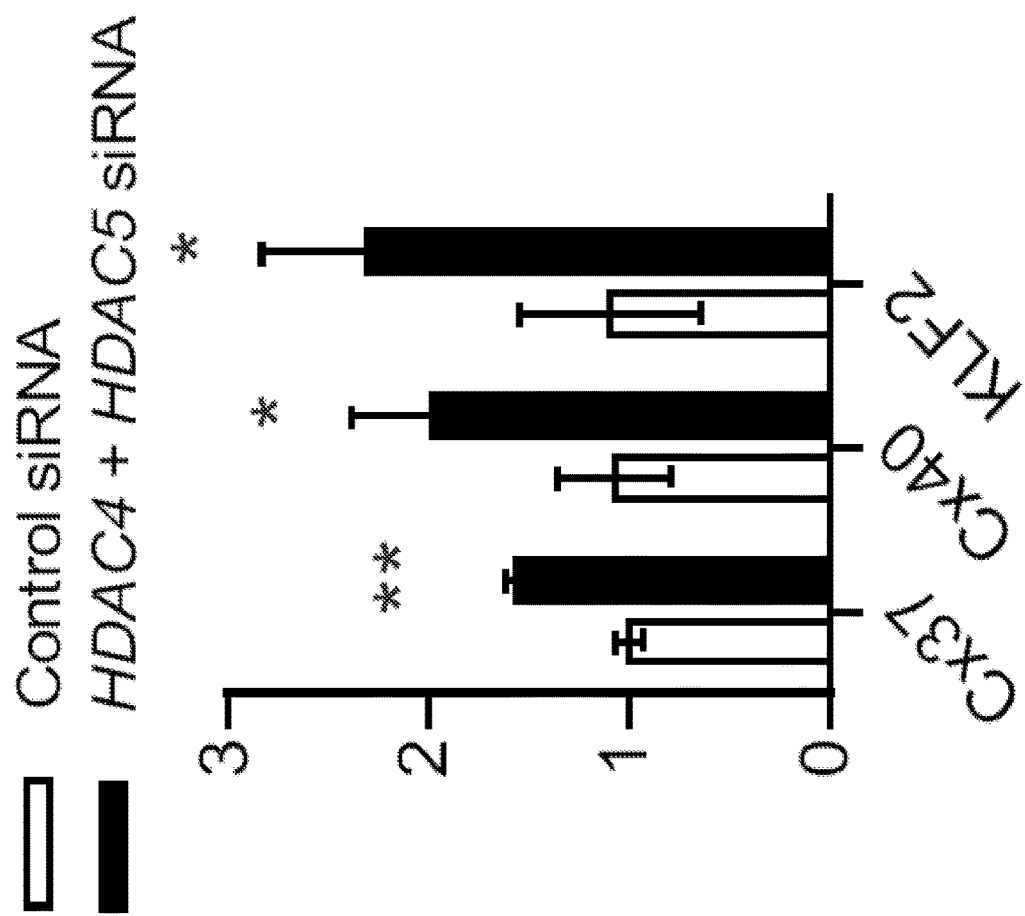
FIG. 7 is a graph showing expression of connexin 37 (Cx37), connexin 40 (Cx40), and KLF2 in response to knockdown of HDAC4 and HDAC5 in PAH PAECs. *P<0.05 and **P<0.01 vs. control siRNA.
Figure 8:
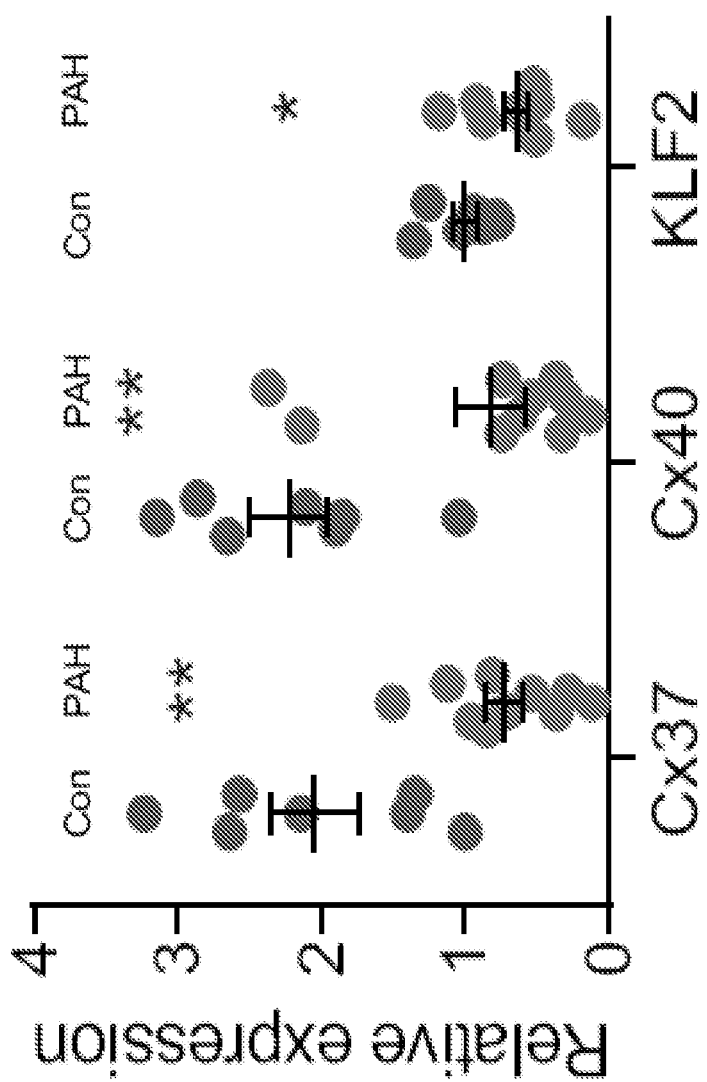
FIG. 8 is a graph showing transcript levels of Cx37, Cx40, and KLF2 in PAECs from controls and PAH patients. *P<0.05 and **P<0.01 vs. control PAECs.

Selective inhibition of HDAC4 and HDAC5 by siRNA mediated knockdown in PAH PAECs led to a significant increase in MEF2 transcriptional targets, including KLF2, connexin 37 (Cx37), and connexin 40 (Cx40) (FIG. 7). PAH PAECs a significantly decreased transcript levels of Cx37, Cx40, and KLF2 compared to controls (FIG. 8), providing further evidence that MEF2 transcriptional activity is reduced in these cells.

Figure 9:
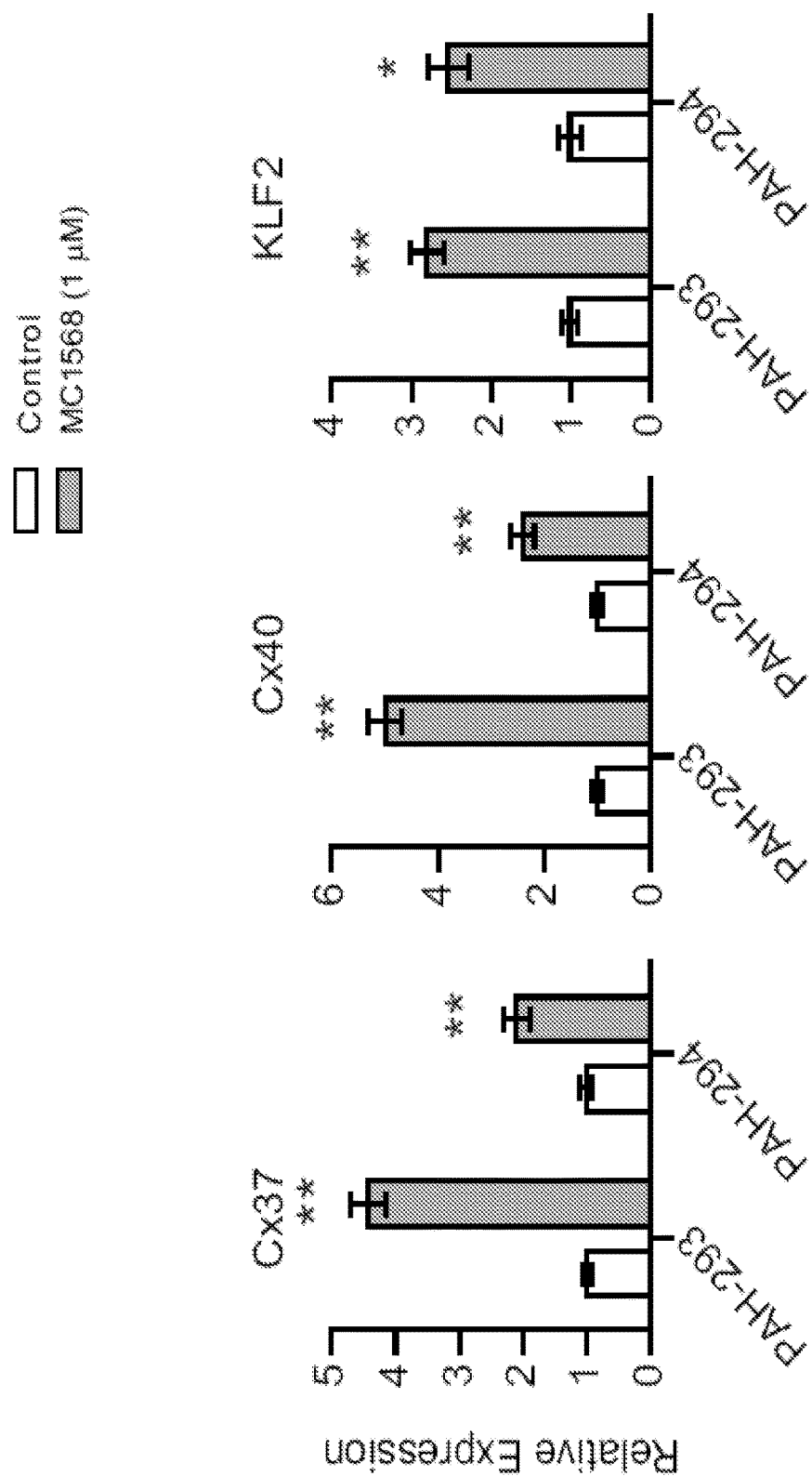
FIG. 9 is a panel of graphs showing relative expression of Cx37, Cx40, and KLF2 in PAH PAECs treated with MC1568 (1 µM for 24 h). *P<0.05 and **P<0.01 vs. control.
Figure 10:
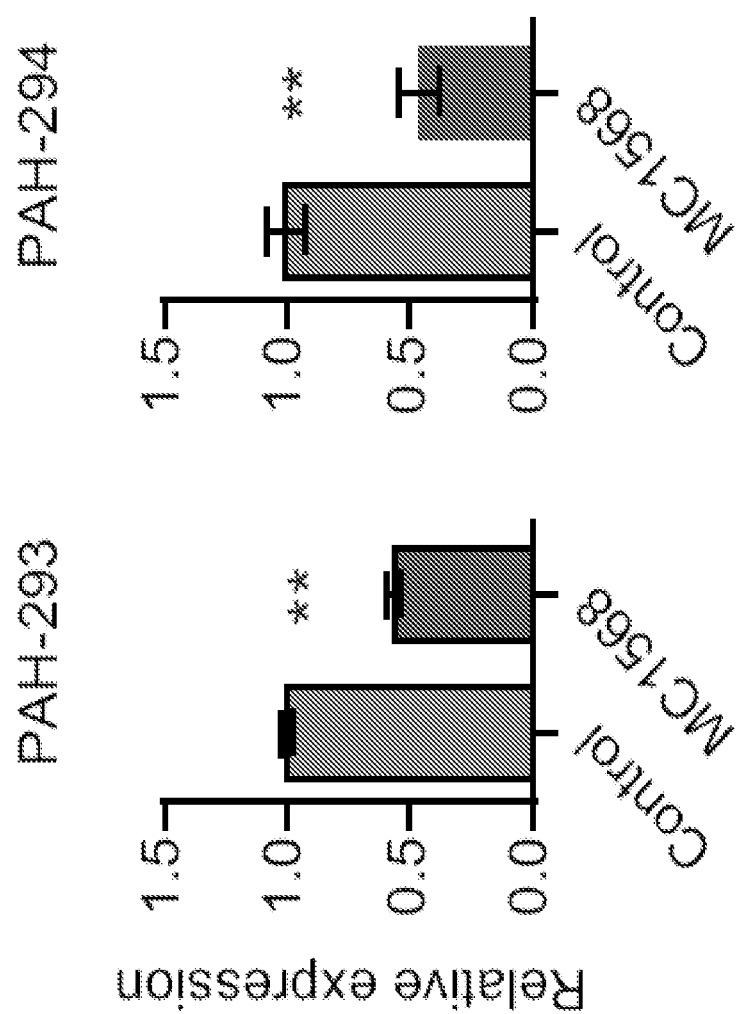
FIG. 10 is a panel of graphs showing relative expression of FGF2 in PAH PAECs treated with MC1568 (1 µM for 24 h). **P<0.01 vs. control.
Figure 11:
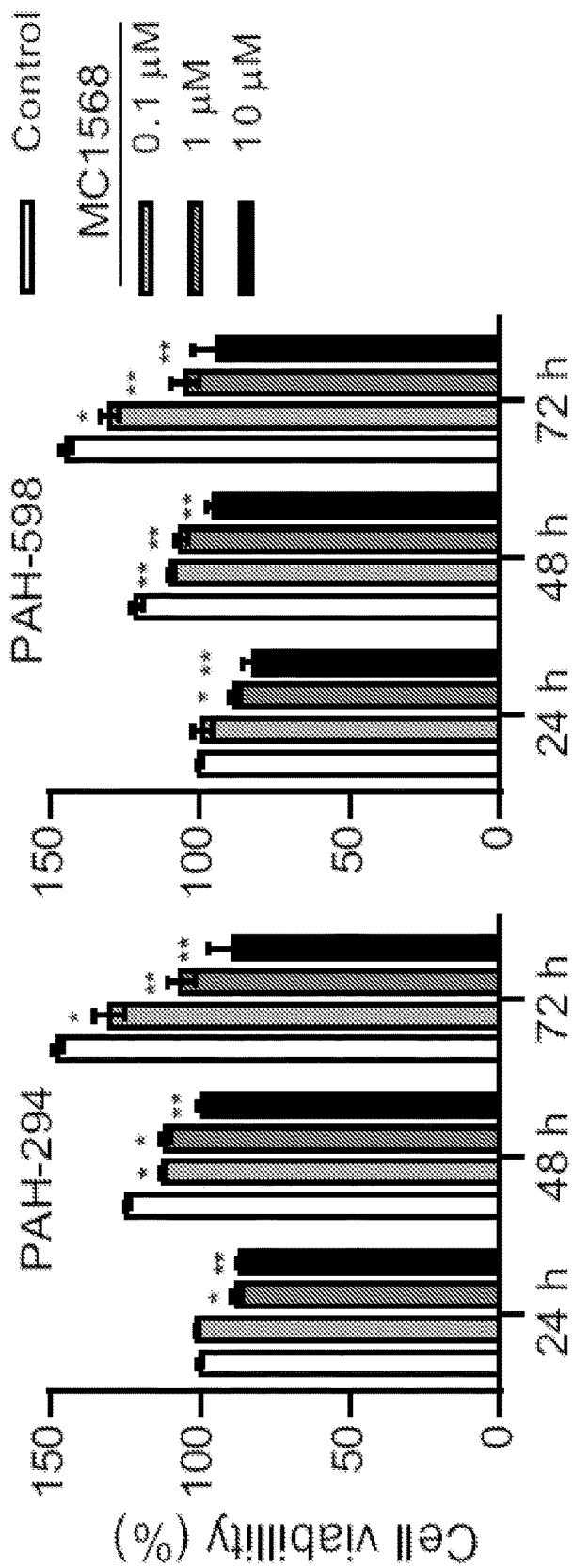
FIG. 11 is a panel of graphs showing proliferation of PAH PAECs in response to MC1568 stimulation. *P<0.05 and **P<0.01 vs. control.
Figure 12B:
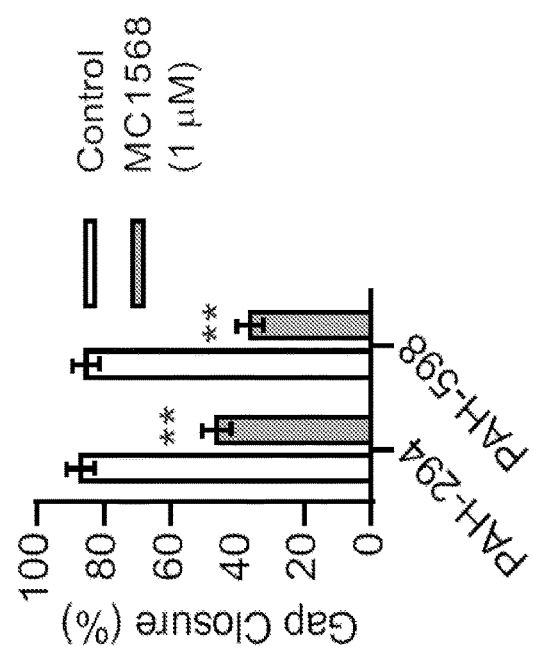
FIG. 12B is a graphs showing PAH PAEC migration in response to MC1568 stimulation. **P<0.01 vs. control.
Figure 12A:
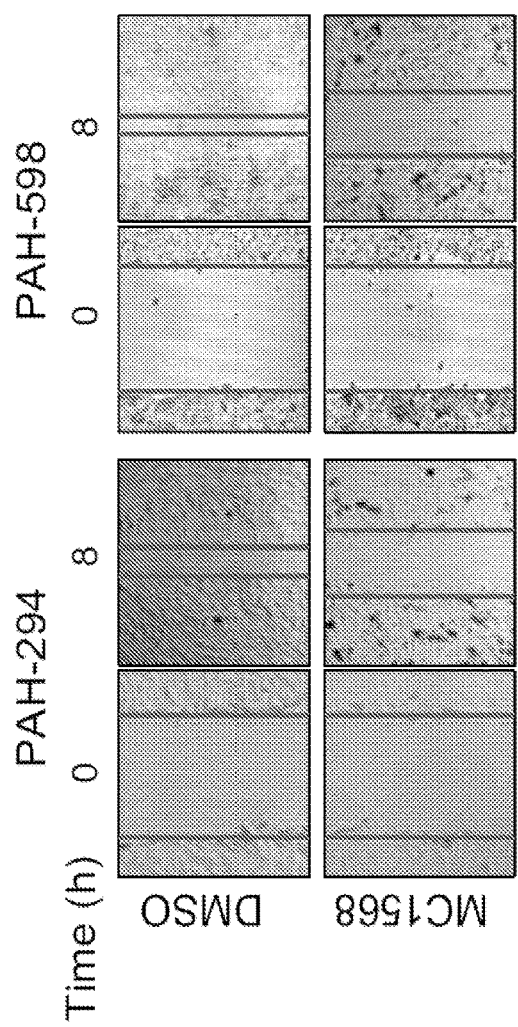
FIG. 12A is a panel of images showing PAH PAEC migration in response to MC1568 stimulation.

The efficacy of a pharmacologic HDAC class IIa specific inhibitor, MC1568, on MEF2 target expression was tested. The (aryloxopropenyl)pyrrolyl hydroxylamine, MC1568, has been demonstrated to have selective inhibition of class IIa HDACs, without affecting other HDAC classes. Treatment of PAH PAECs with MC1568 resulted in significant increased expression of Cx37, Cx40, and KLF2 (FIG. 9). Moreover, treatment of PAH PAECs with MC1568 leads to a significant downregulation of FGF2 and aberrantly increased in PAH PAECs (FIG. 10). MC1568 treatment also led to significant reduction of PAH PAEC proliferation (FIG. 11) and migration (FIGS. 12A and 12B).

Figure 13:
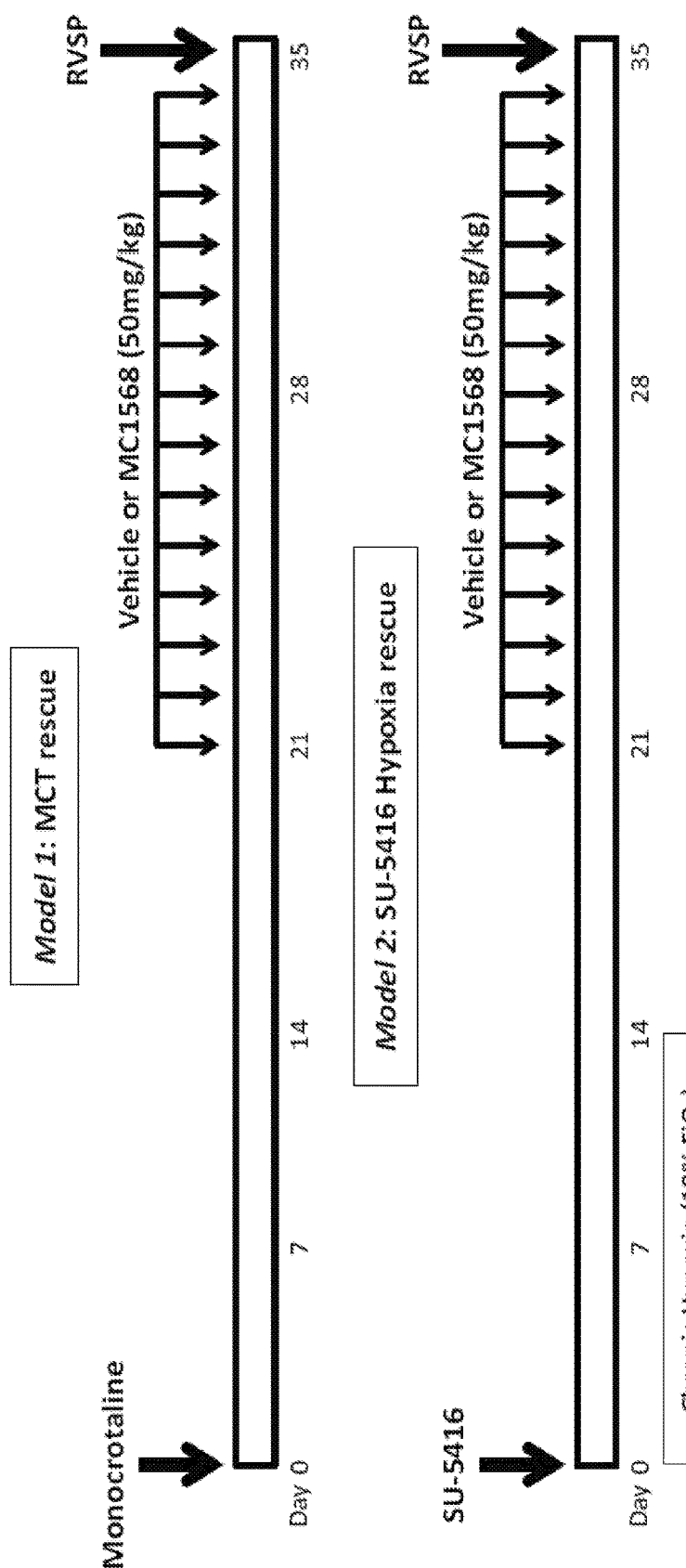
FIG. 13 is a schematic illustration of the experimental pulmonary hypertension model used in the experiments.
Figure 14:
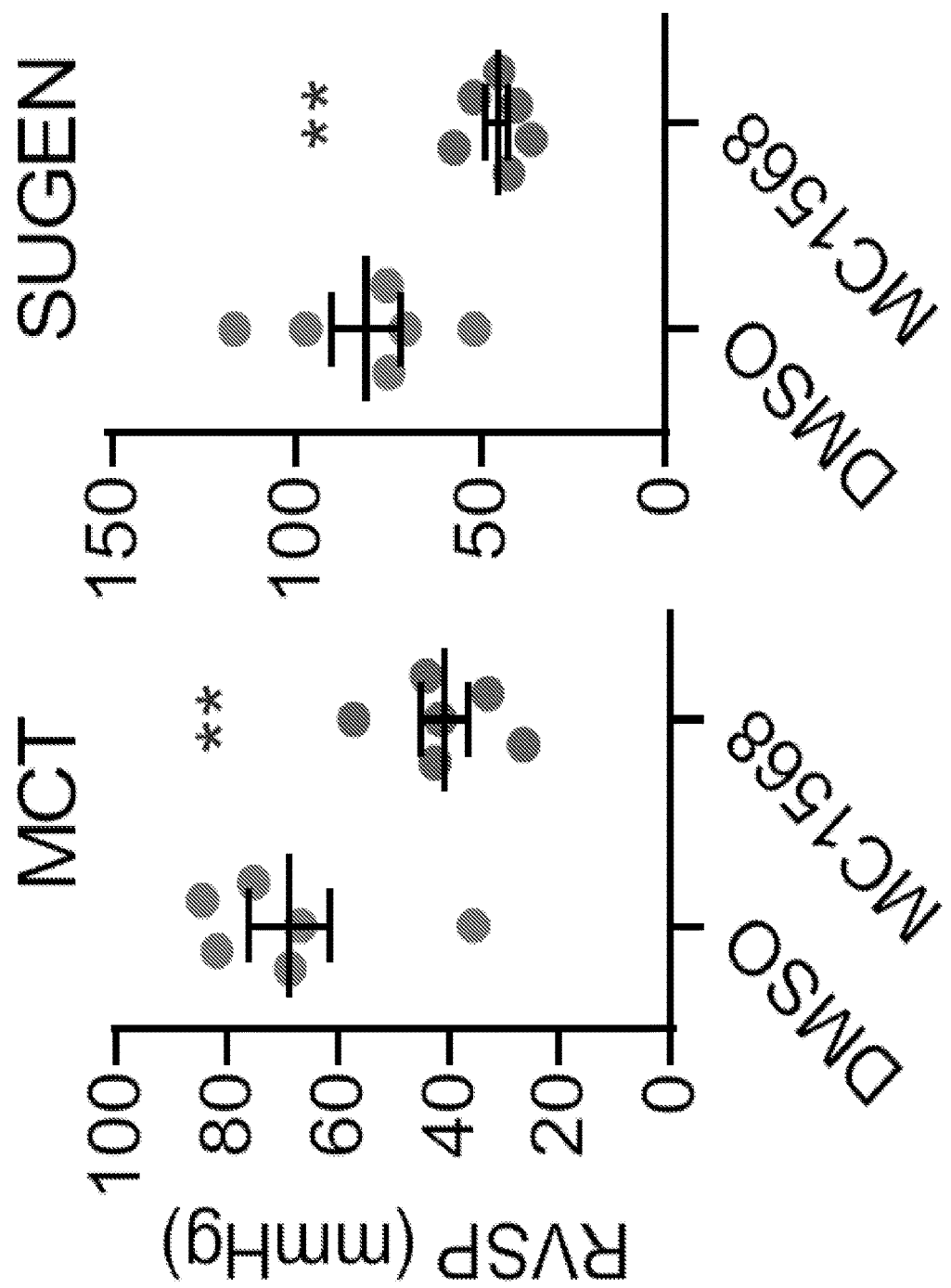
FIG. 14 is a panel of graphs showing right ventricular systolic pressure (RVSP) measurement in rats receiving either vehicle (DMSO) or MC1568 in the monocrotaline (MCT) and SU-5416/hypoxia (SUGEN) models. **P<0.01 vs. vehicle treated rats.
Figure 15:
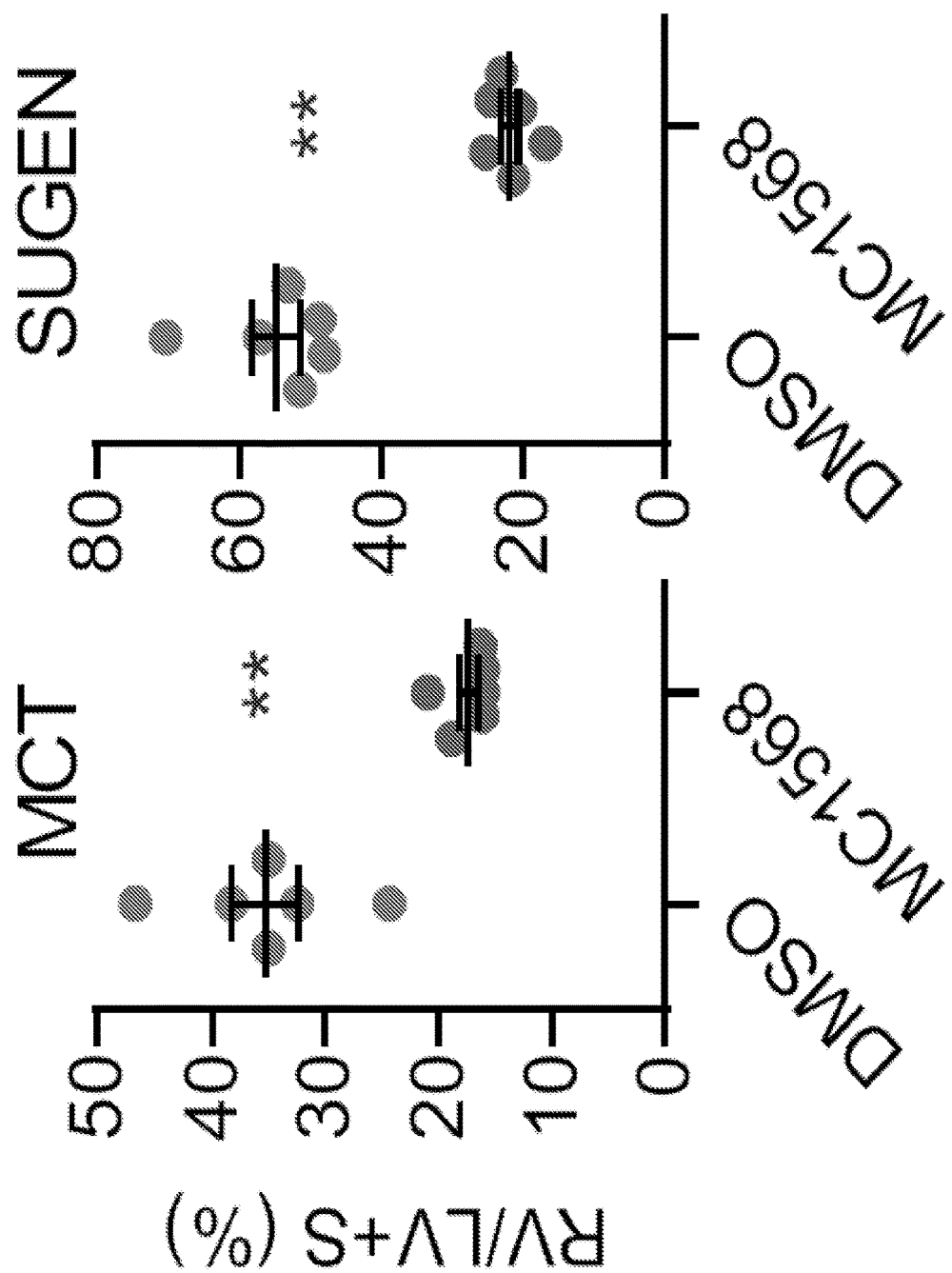
FIG. 15 is a panel of graphs showing right ventricle to left ventricle+septum (RV/LV+S) weight ratios in the MCT and SUGEN models with either vehicle (DMSO) or MC1568 treatment. **P<0.01 vs. vehicle treated rats.
Figures 16A, 16B:
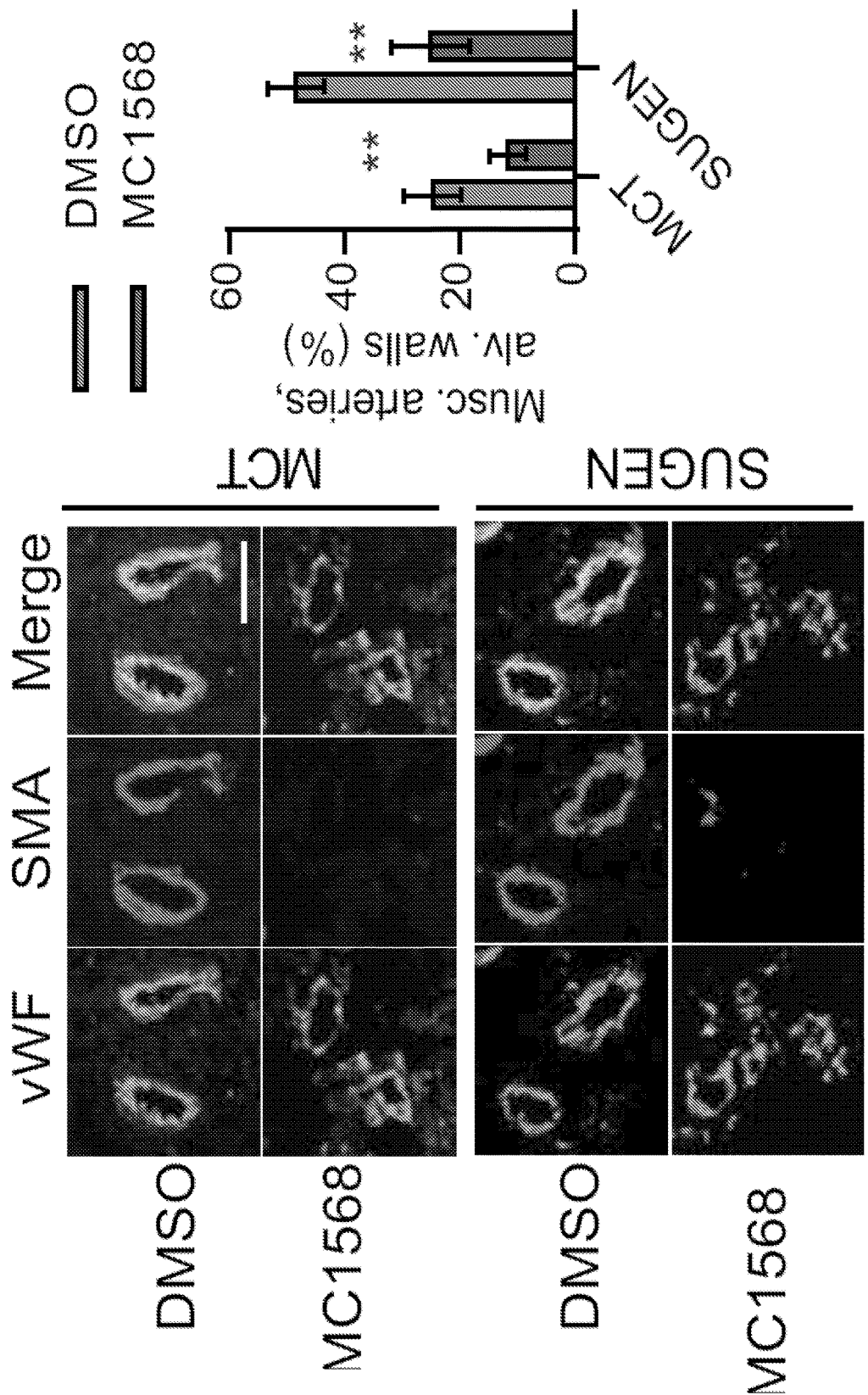
FIG. 16A is a panel of images showing muscularization (musc.) analysis of the pulmonary arterioles in the alveolar (alv.) wall of lungs from rats receiving either vehicle (DMSO) or MC1568 in the two experimental PH models. Smooth-muscle actin (SMA) is shown in the middle column, von Willebrand Factor (vWF) is shown in left column, and merged SMA and vWF is shown in the right column. Scale bar: 50 µm.
FIG. 16B is a graph showing the percentage of muscularization (musc.) analysis of the pulmonary arterioles in the alveolar (alv.) wall of lungs from rats receiving either vehicle (DMSO) or MC1568 in the two experimental PH models **P<0.01 vs. vehicle treated rats in each model.
Figure 18:
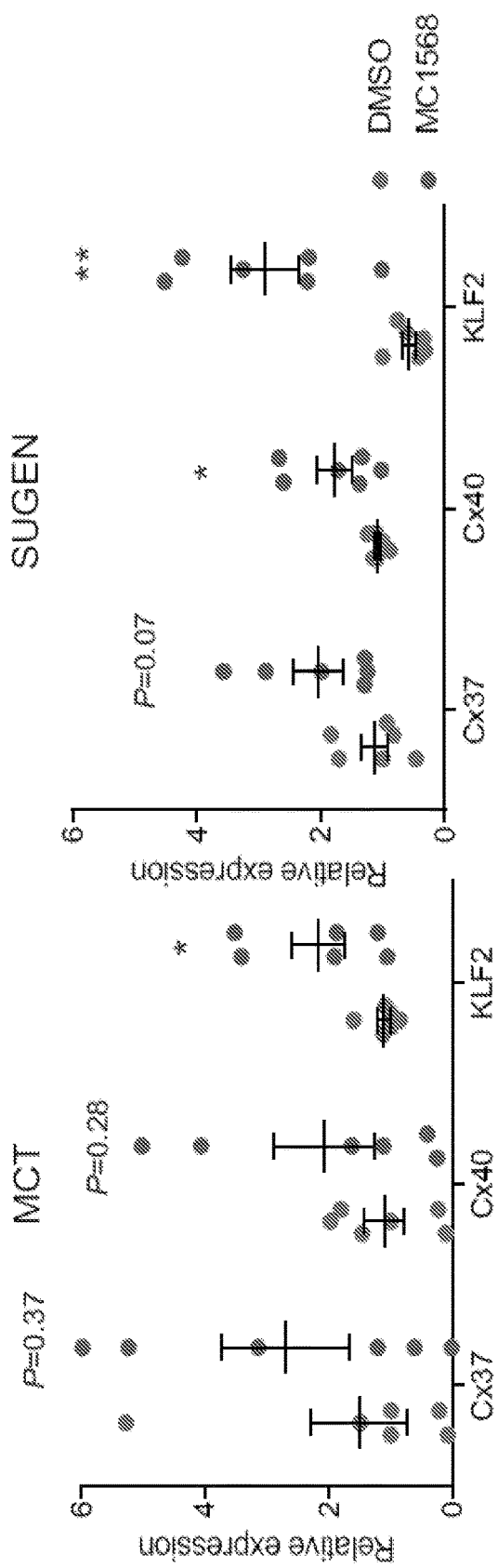
FIG. 18 is a panel of graphs showing expression levels of putative MEF2 transcriptional targets in PH models tested. *P<0.05 and **P<0.01 vs. DMSO.
Figure 19:
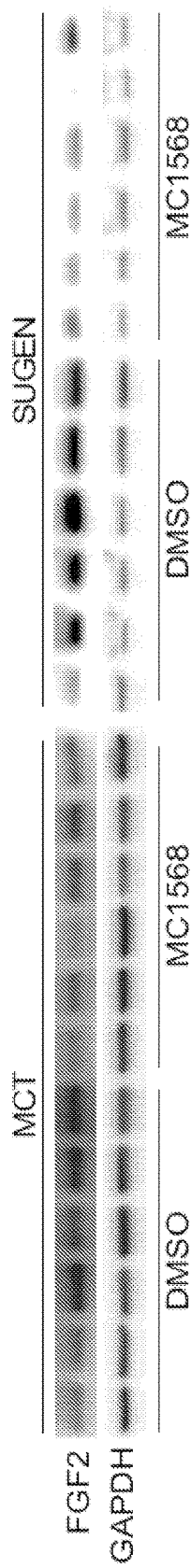
FIG. 19 is a panel of blots showing FGF2 protein expression in lung homogenates of rats in the two PH models in response to MC1568 treatment.

Given the in vitro findings demonstrating the effects of MC1568, two experimental PH models (monocrotaline (MCT) and SU-5416/hypoxia (SUGEN)) were tested to determine the efficacy of MC1568 in reversing established PH in rats (FIG. 13). Measurement of the right ventricular systolic pressures (RVSP) demonstrated a significant decrease in MC1568 administered rats compared to controls in both the MCT and the SUGEN models (FIG. 14). A significant reduction in the right ventricle to left ventricle+ septum weight ratios in the MC1568 groups (FIG. 15). Morphometric lung studies demonstrated a significantly decreased muscularization of small arterioles in the MC1568 groups (FIGS. 16A and 16B). Moreover, PCNA-positive proliferating vascular cells were significantly fewer in MC1568 treated groups compared to control groups (FIGS. 17A and 17B). Moreover, other MEF2 transcriptional targets (Cx37, Cx40 and KLF2) were also increased in the MC1568 treated groups (FIG. 18). Lastly, expression of FGF2 was significantly decreased in the lungs of MC1568 administered rats (FIG. 19).

Figure 20:
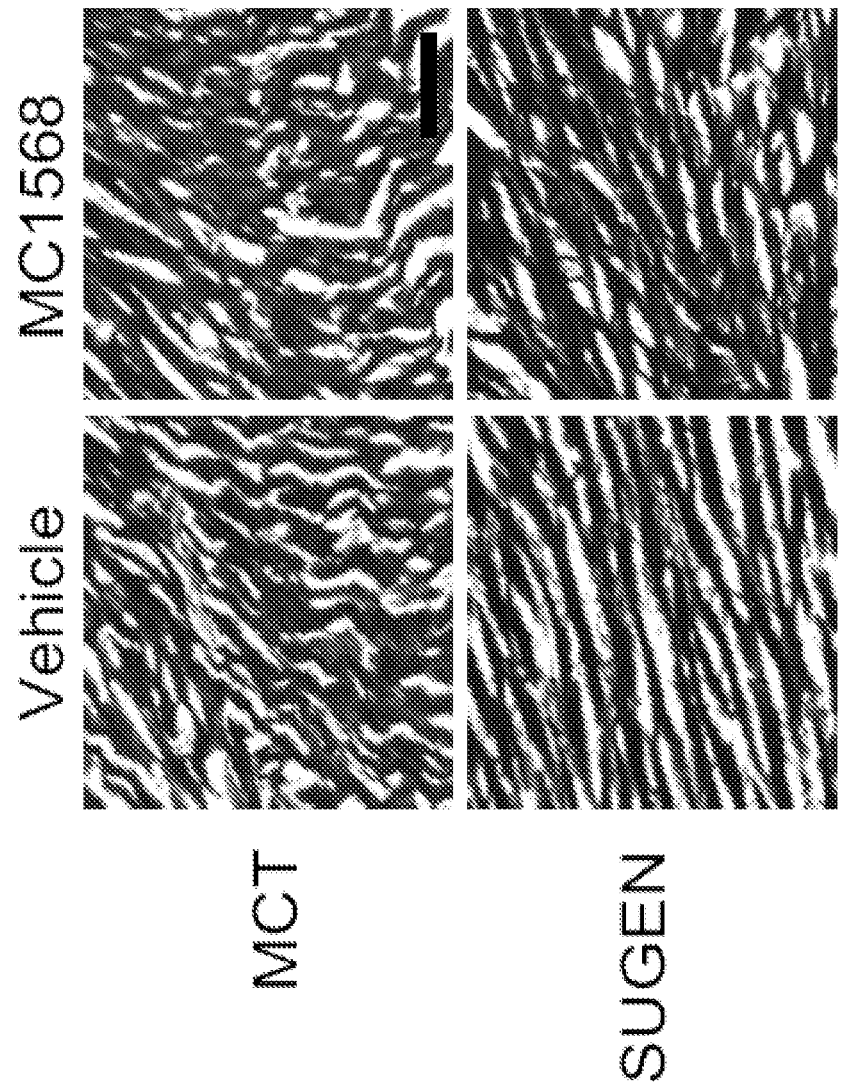
FIG. 20 is a panel of images showing trichrome staining of the right ventricle from the four treatment groups. Scale bar: 100 µm.
Figure 21:
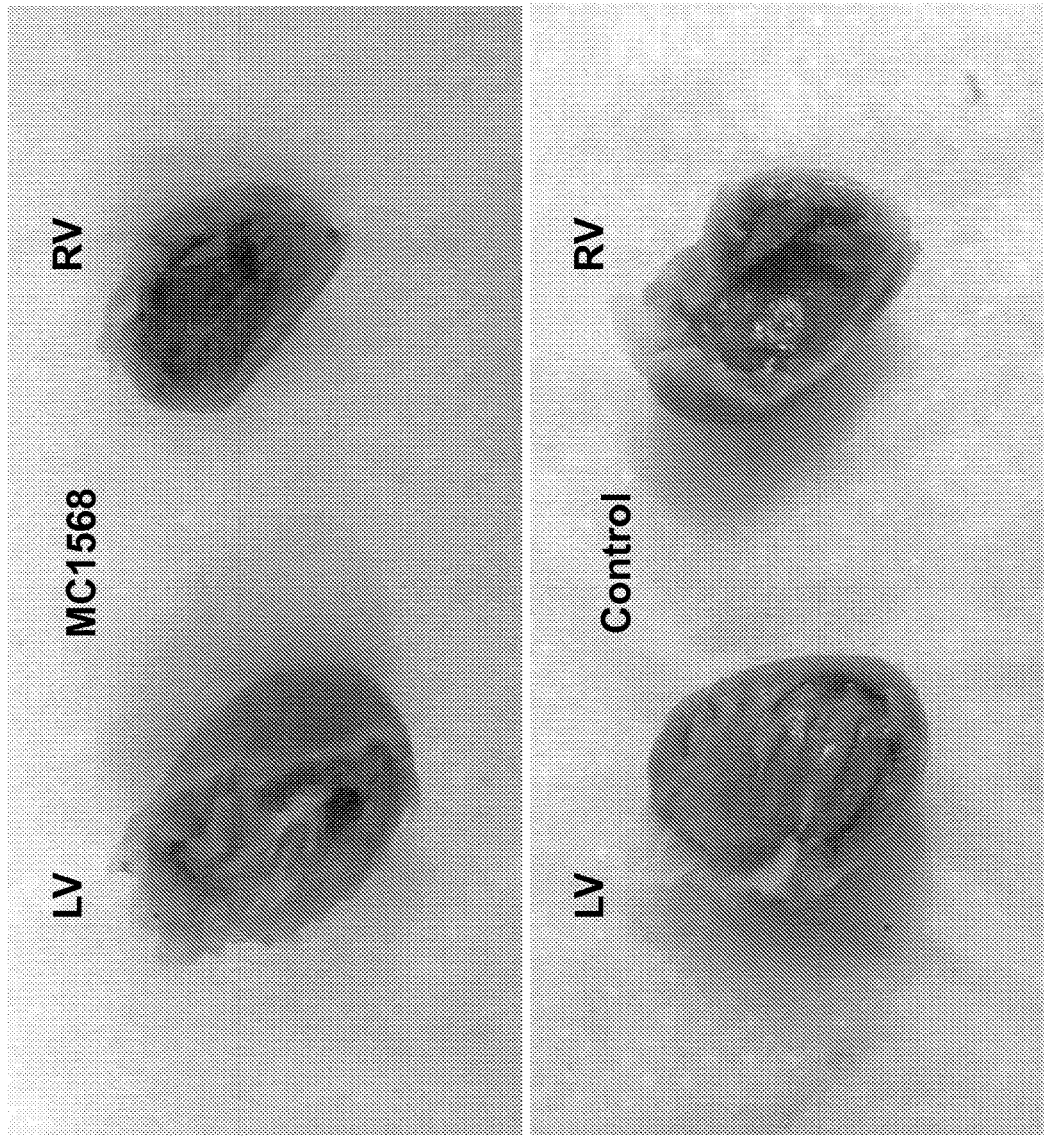
FIG. 21 is a panel of images showing gross histology of the left ventricles (LV) and right ventricles (RV) in MC1568 treated groups compared to control groups.
Figure 22:
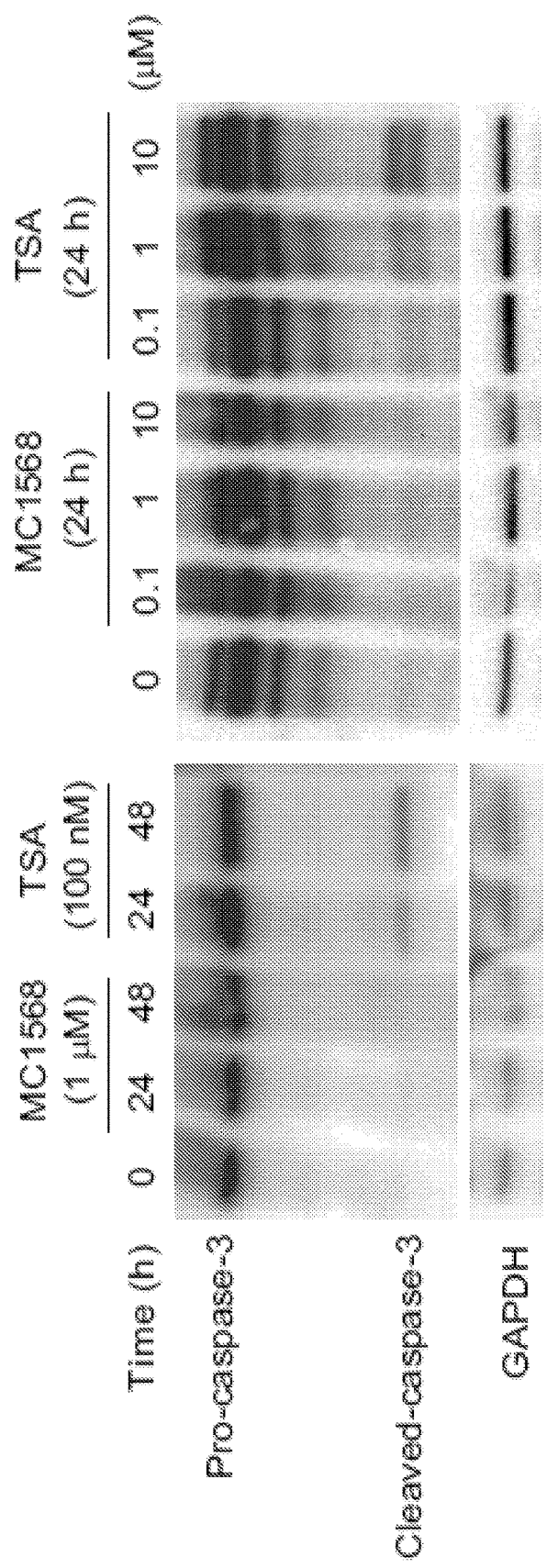
FIG. 22 is a panel of blots showing the effects of MC1568 or trichostatin A (TSA) on caspase 3 cleavage in human coronary artery endothelial cells.

A previous study suggested that global HDAC inhibition, via administration of trichostatin A (TSA) and valproic acid, results in detrimental injury to the right ventricle in the context of pulmonary artery banding. Selective HDAC class IIa inhibition was evaluated to determine if it can potentially avoid the deleterious cardiac effects seen with broader HDAC inhibition. Unlike what has been described with TSA, no evidence of myocardial fibrosis in rats receiving MC1568 in both the MCT and SUGEN groups (FIGS. 20 and 21). Moreover, treatment of human coronary artery endothelial cells with TSA, a broad spectrum HDAC inhibitor, lead to marked induction of cellular apoptosis as assessed by caspase 3 cleavage, while MC1568 treatment did not result in caspase activation (FIG. 22).

Overall, these findings provide key support for selective targeting of class IIa HDACs in PAH, by: 1) identifying key transcriptional and functional effects of HDAC IIa inhibition in PAECs, 2) defining MEF2 as a key class IIa HDAC binding partner and the transcription factor whose function is compromised in PAH PAECs, and 3) demonstrating that inhibition of class IIa HDACs can robustly rescue PH in experimental models while avoiding the potential detrimental effects on the right ventricle. These findings define a novel signaling paradigm that may be critically important as new treatment strategies in PAH are pursued, while minimizing the adverse effects. The recent emergence of additional selective HDAC class IIa targeting inhibitors should facilitate the testing of this promising therapeutic target.

Figure 23:
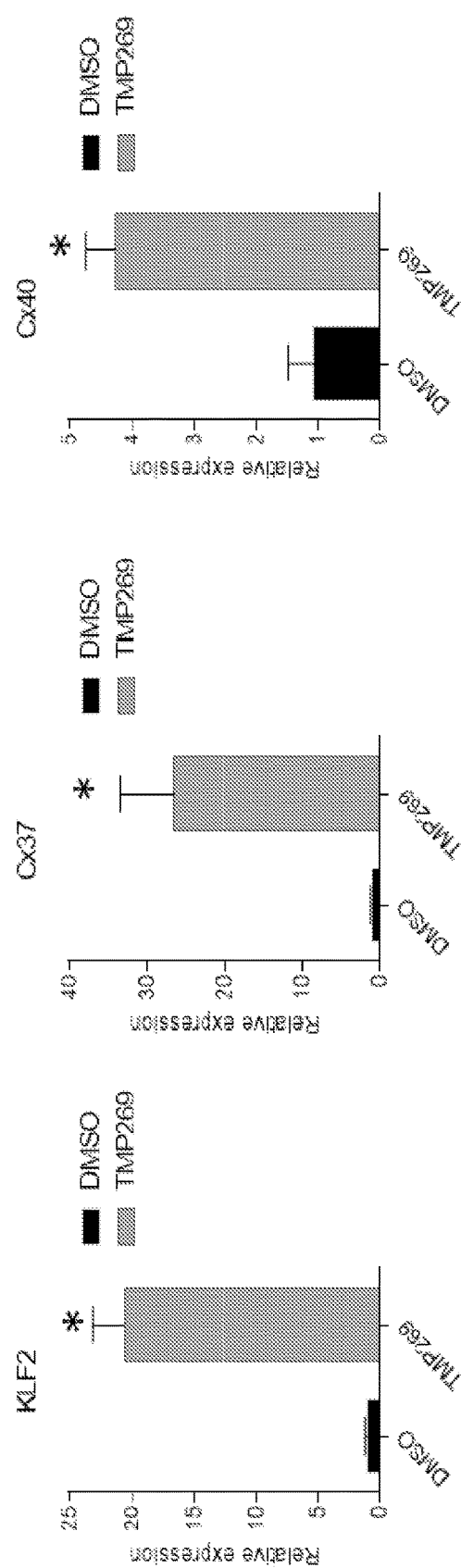
FIG. 23 is a panel of graphs showing that treatment of pulmonary arterial endothelial cells from a PAH patient with TMP269 induced MEF2 transcriptional targets (*P<0.01).
Figure 24:
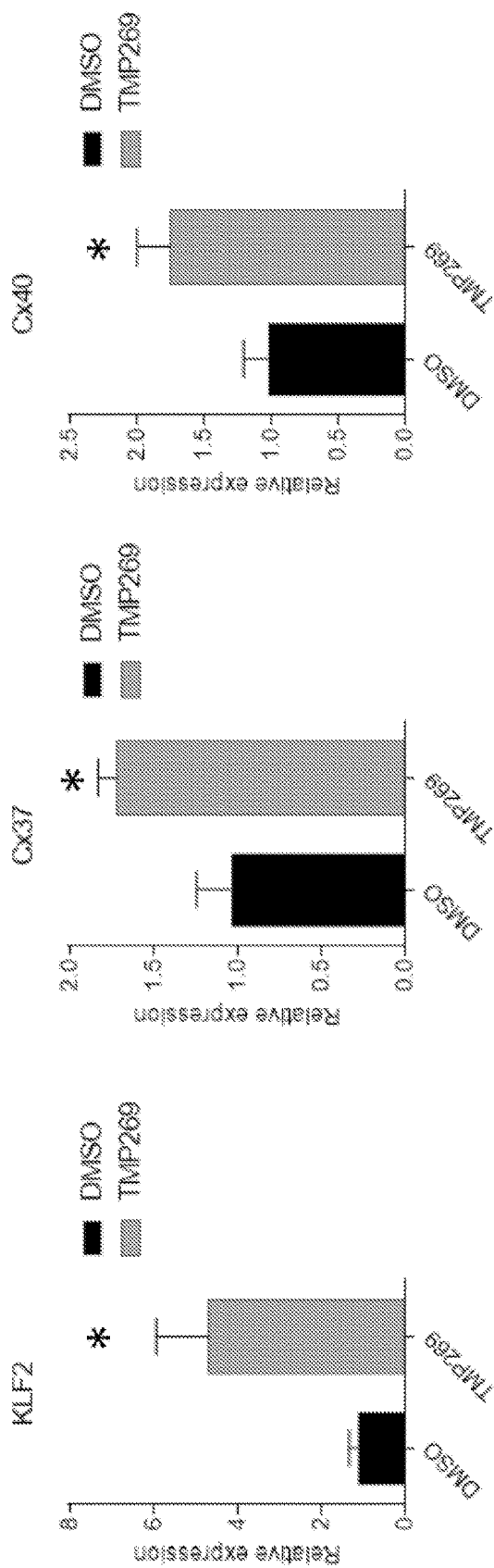
FIG. 24 is a panel of graphs showing that treatment of pulmonary arterial endothelial cells from a second PAH patient with TMP269 induced MEF2 transcriptional targets (*P<0.01).

Example 2: Testing Efficacy of Histone Deacetylase Inhibition with TMP269 or Tasquinimod in Pulmonary Hypertension Pulmonary arterial endothelial cells from two PAH patients were treated with 1 µM TMP269 for 24 hours. MEF2 transcriptional targets, KLF2, Cx37 and Cx40, were significantly increased in the treated cells as compared to the control or DMSO treated cells (*P<0.01), see FIGS. 23 and 24.

Figure 25:
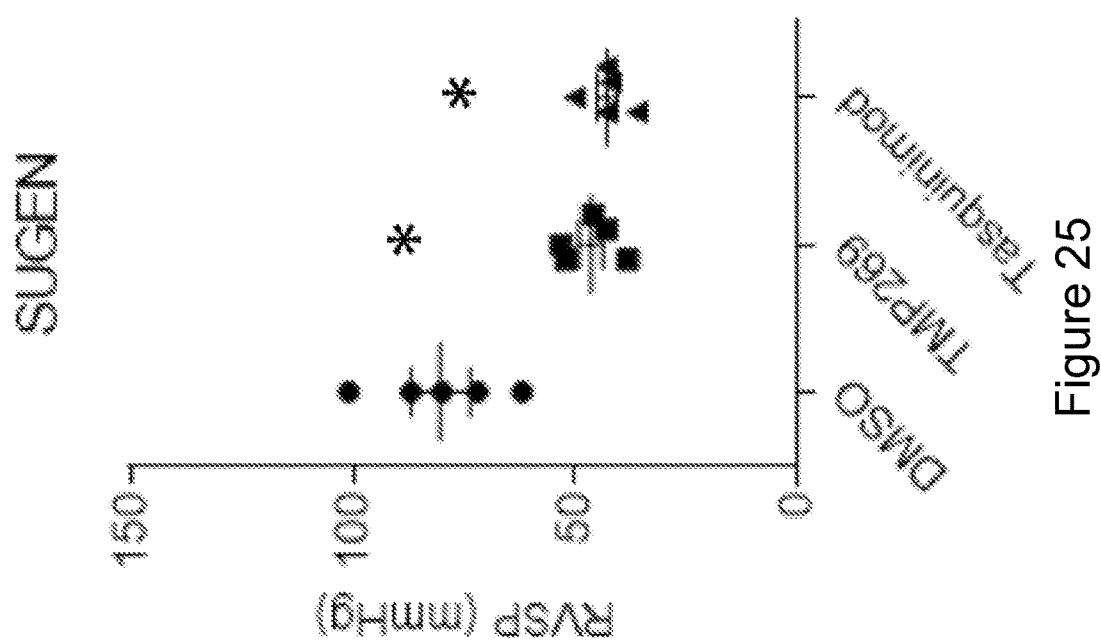
FIG. 25 is a graph showing that both TMP269 and Tasquinimod robustly rescued the SU-5416/hypoxia model of pulmonary hypertension in rats (*P<0.05 vs. control).
Figure 26:
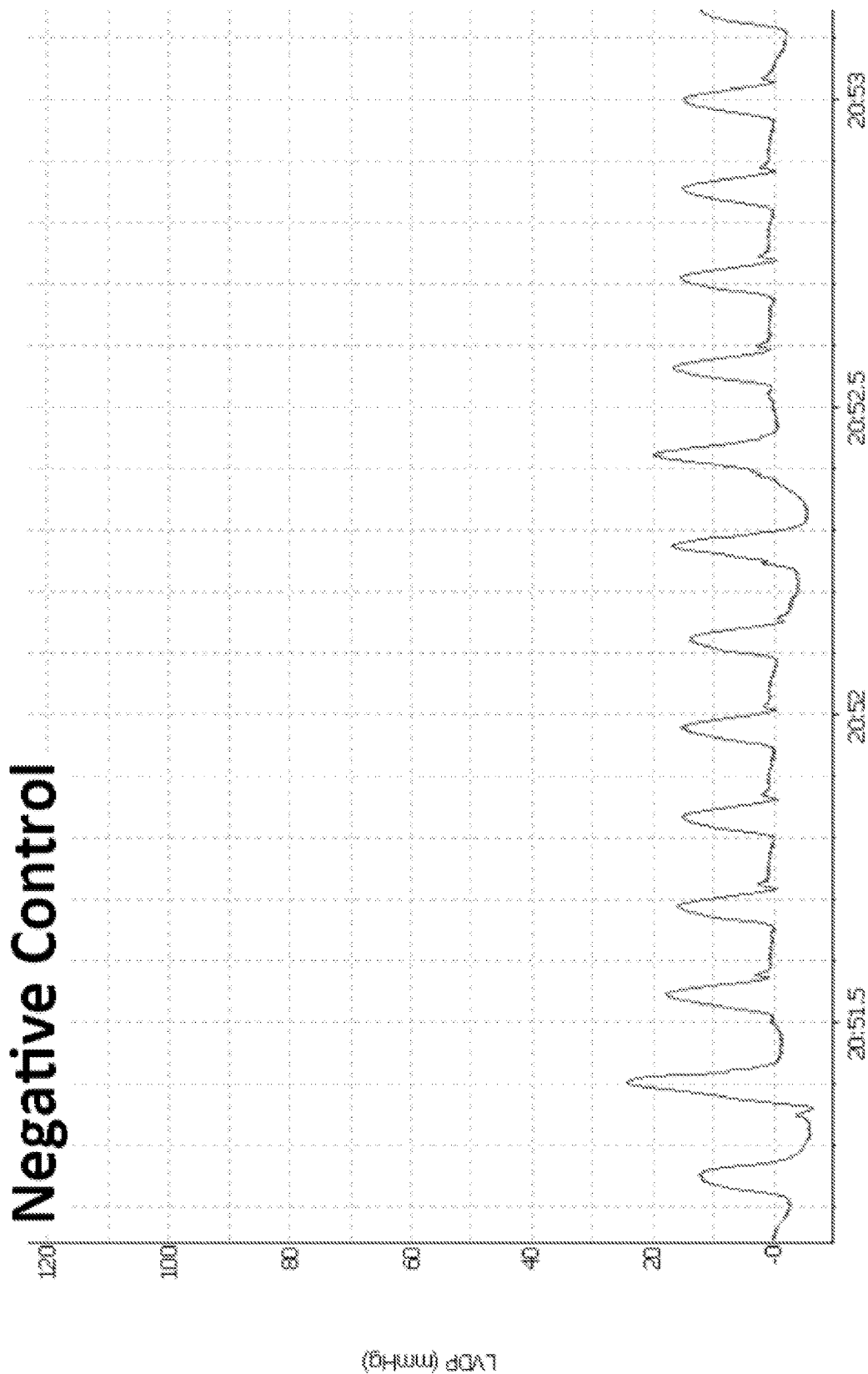
FIG. 26 is a graph showing right ventricular systolic pressure of control rats.
Figure 27:
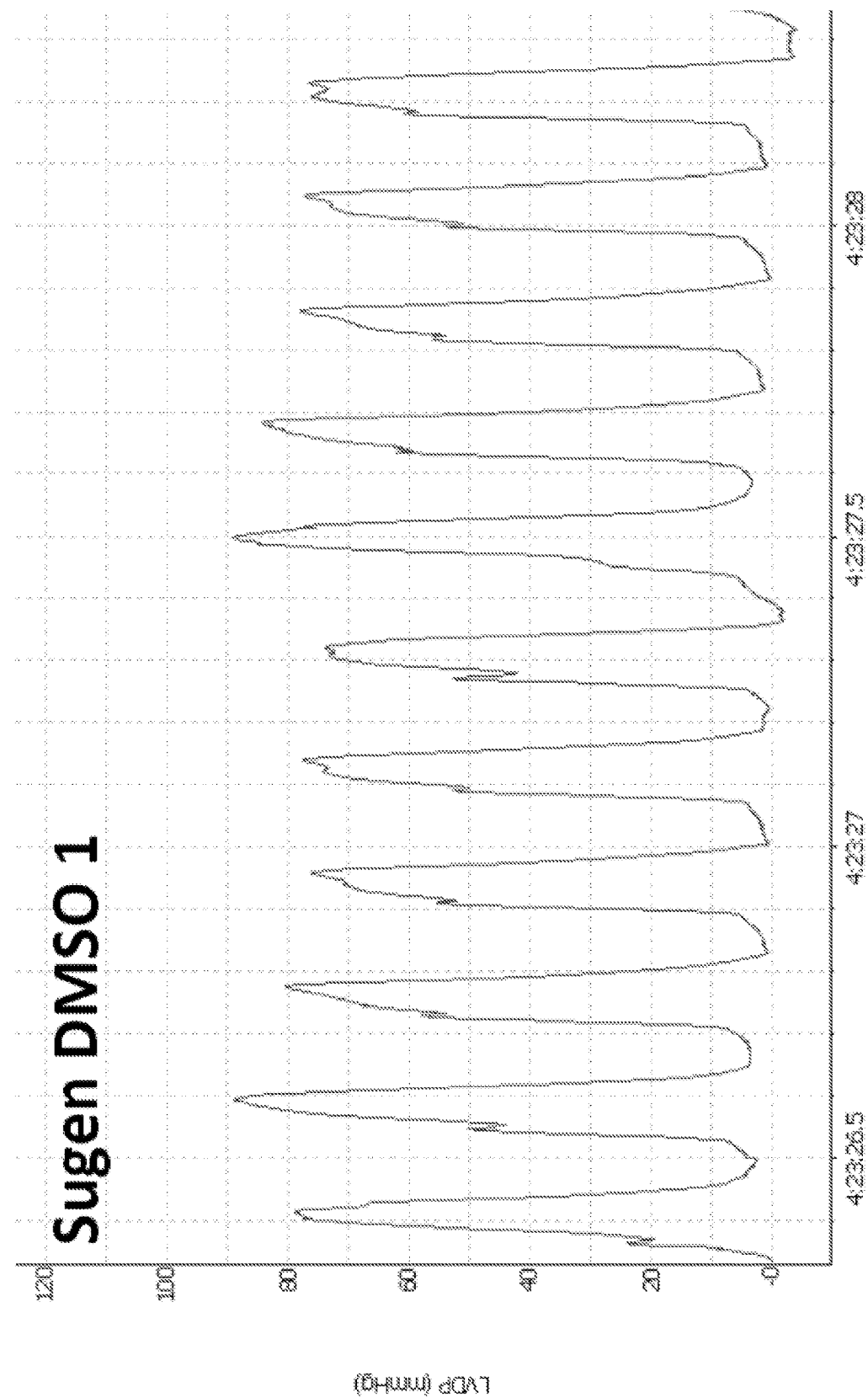
FIG. 27 is a graph showing right ventricular systolic pressure of a rat with pulmonary hypertension treated with DMSO, 1.
Figure 28:
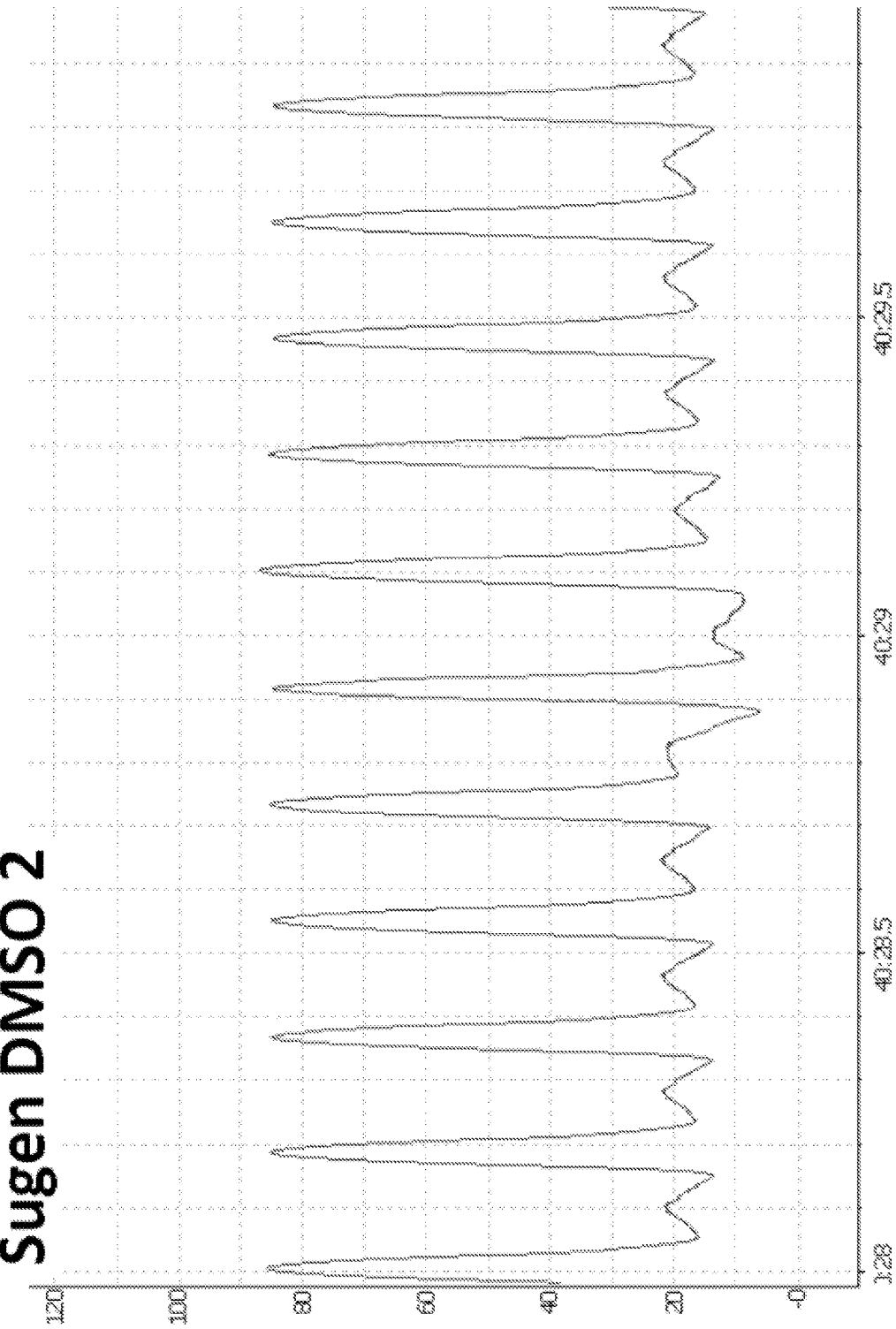
FIG. 28 is a graph showing right ventricular systolic pressure of a rat with pulmonary hypertension treated with DMSO, 2.
Figure 29:
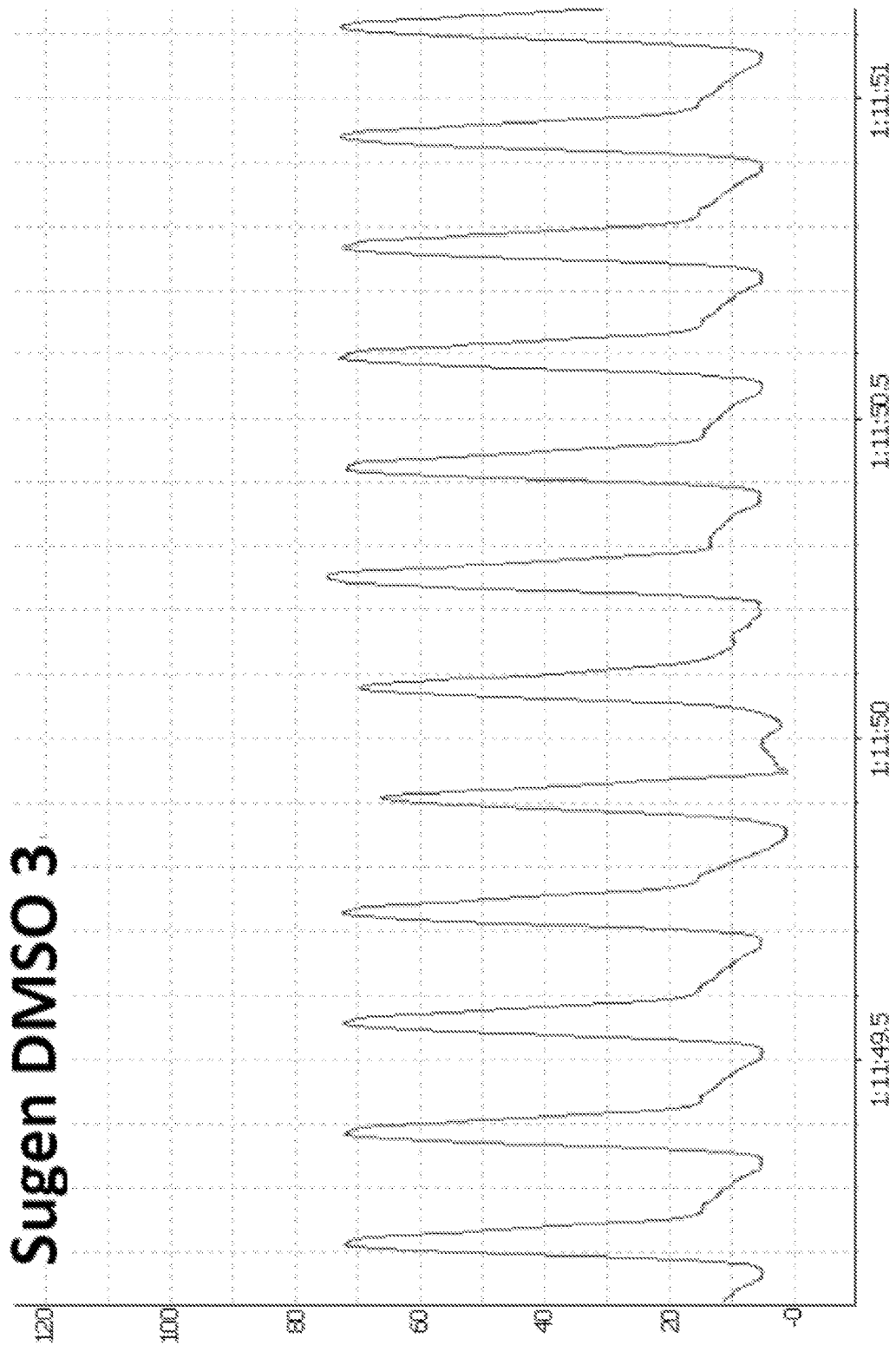
FIG. 29 is a graph showing right ventricular systolic pressure of a rat with pulmonary hypertension treated with DMSO, 3.
Figure 30:
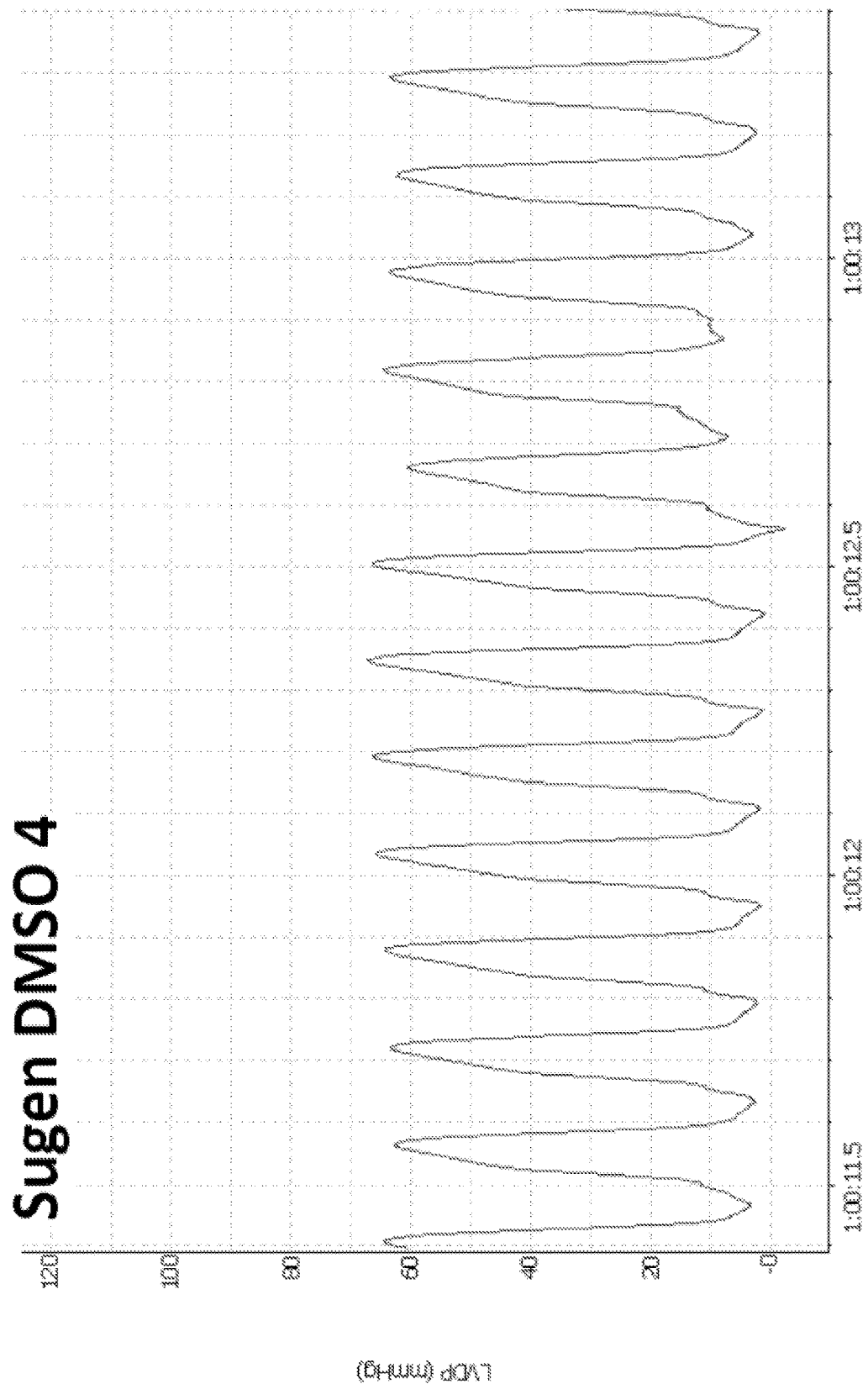
FIG. 30 is a graph showing right ventricular systolic pressure of a rat with pulmonary hypertension treated with DMSO, 4.
Figure 31:
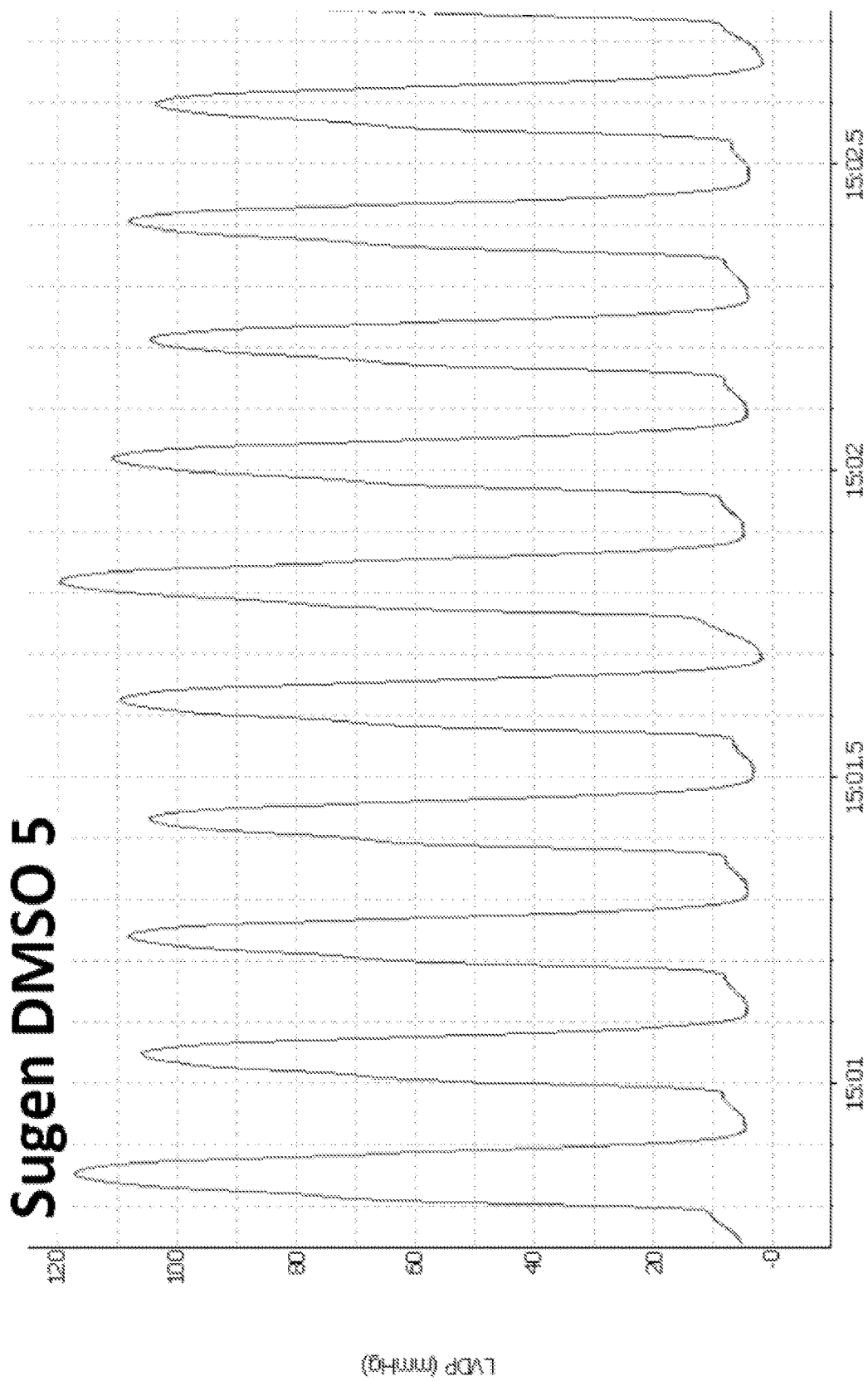
FIG. 31 is a graph showing right ventricular systolic pressure of a rat with pulmonary hypertension treated with DMSO, 5.
Figure 32:
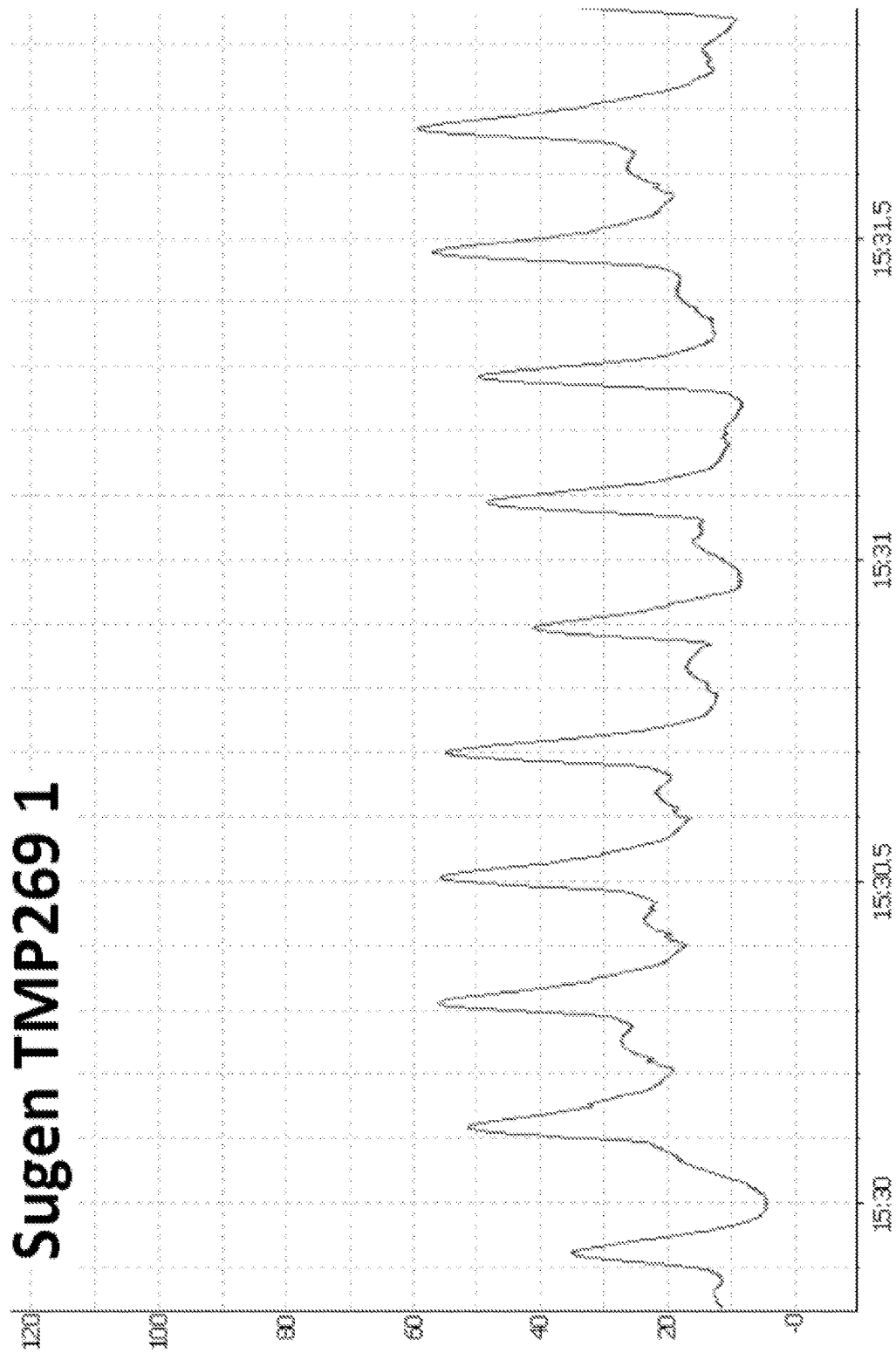
FIG. 32 is a graph showing right ventricular systolic pressure of a rat with pulmonary hypertension treated with TMP269, 1.
Figure 33:
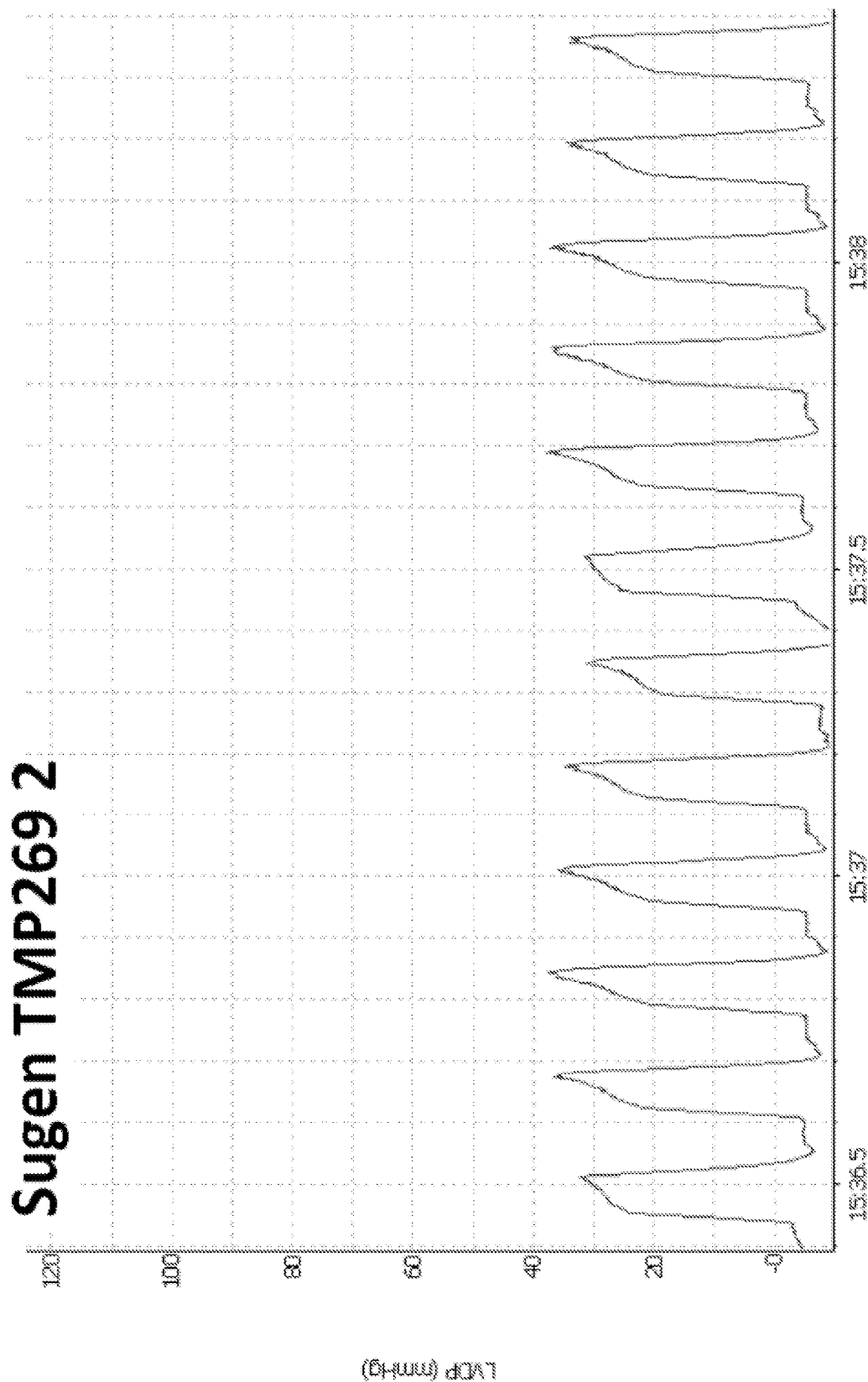
FIG. 33 is a graph showing right ventricular systolic pressure of a rat with pulmonary hypertension treated with TMP269, 2.
Figure 34:
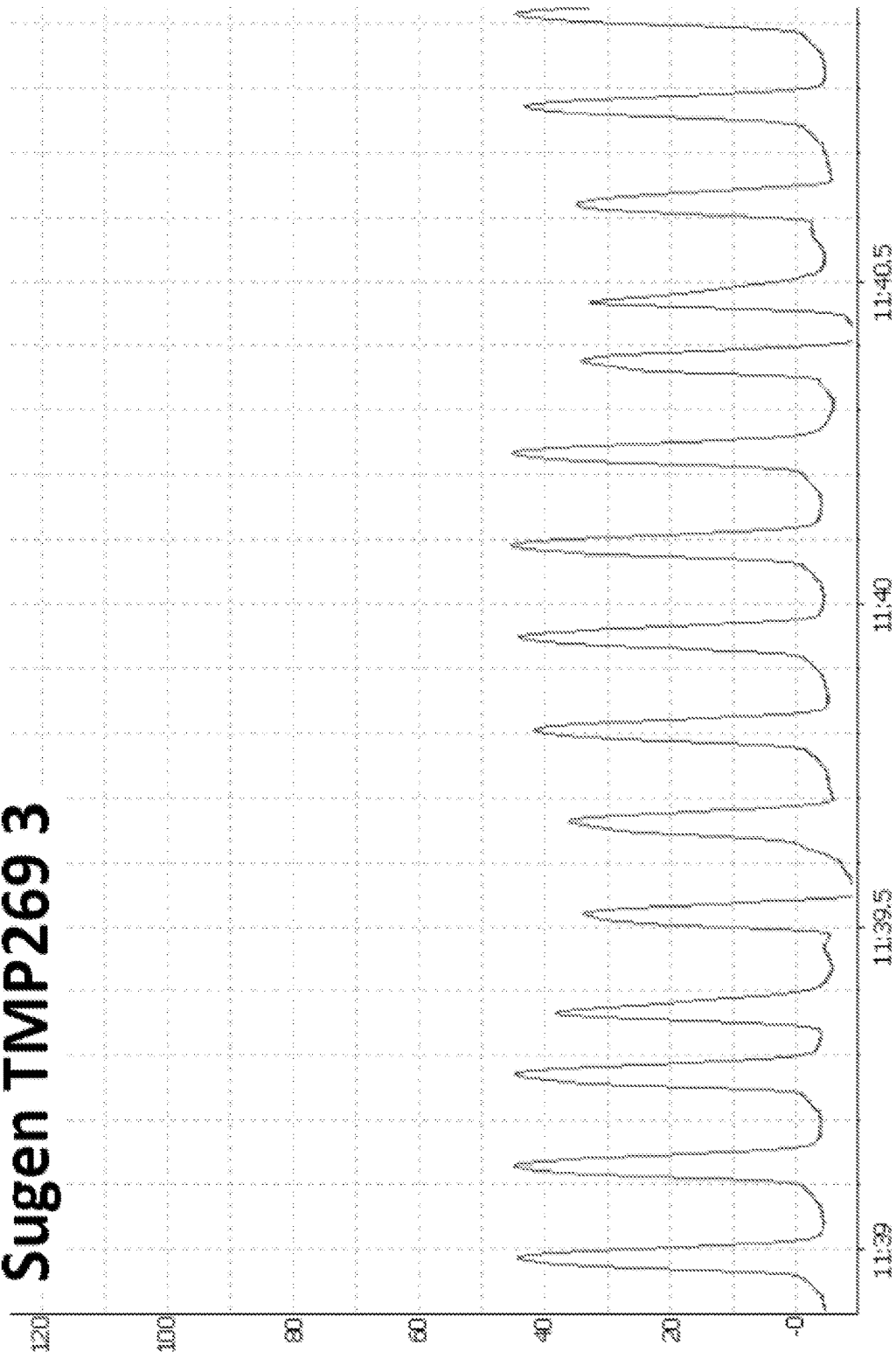
FIG. 34 is a graph showing right ventricular systolic pressure of a rat with pulmonary hypertension treated with TMP269, 3.
Figure 35:
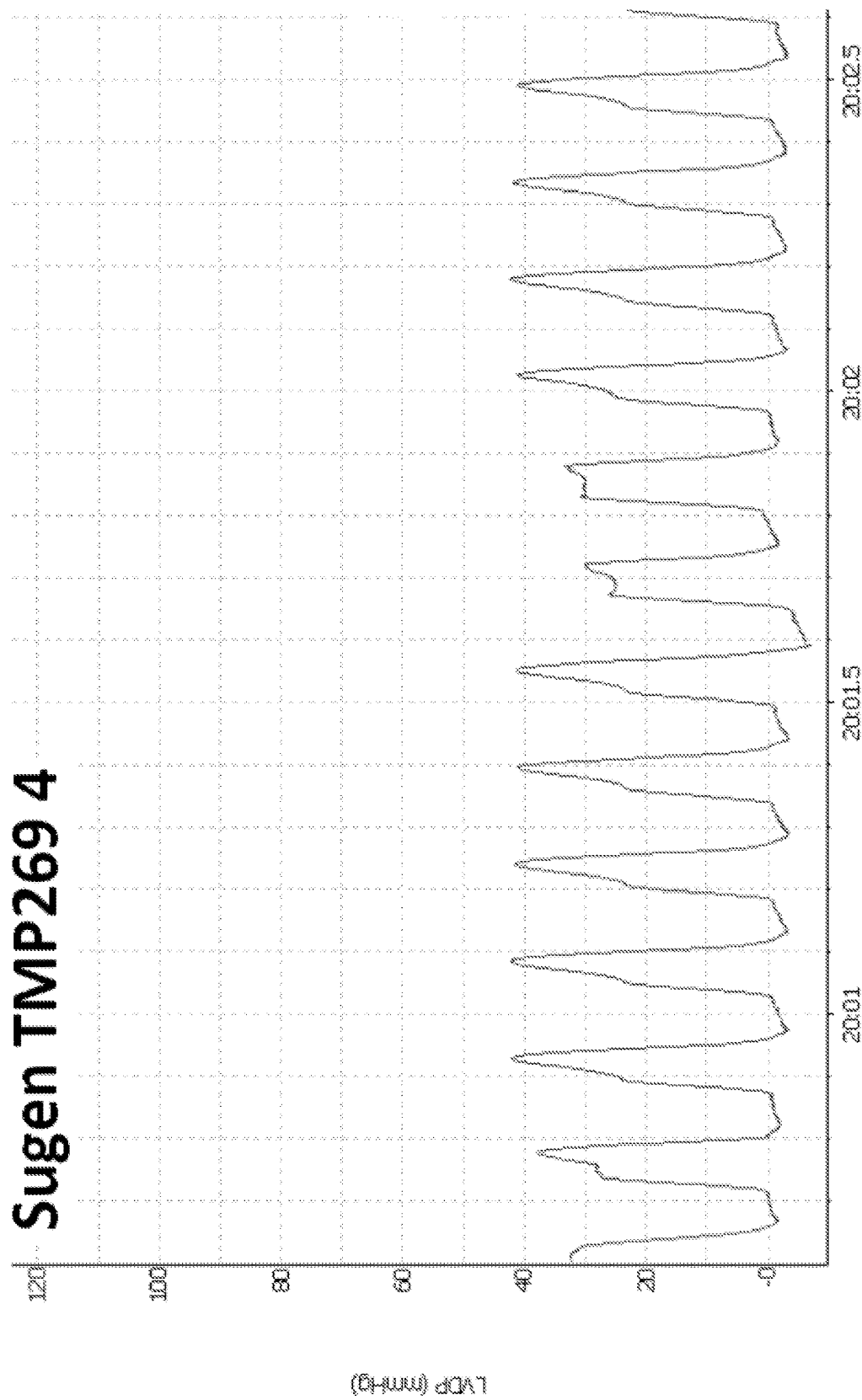
FIG. 35 is a graph showing right ventricular systolic pressure of a rat with pulmonary hypertension treated with TMP269, 4.
Figure 36:
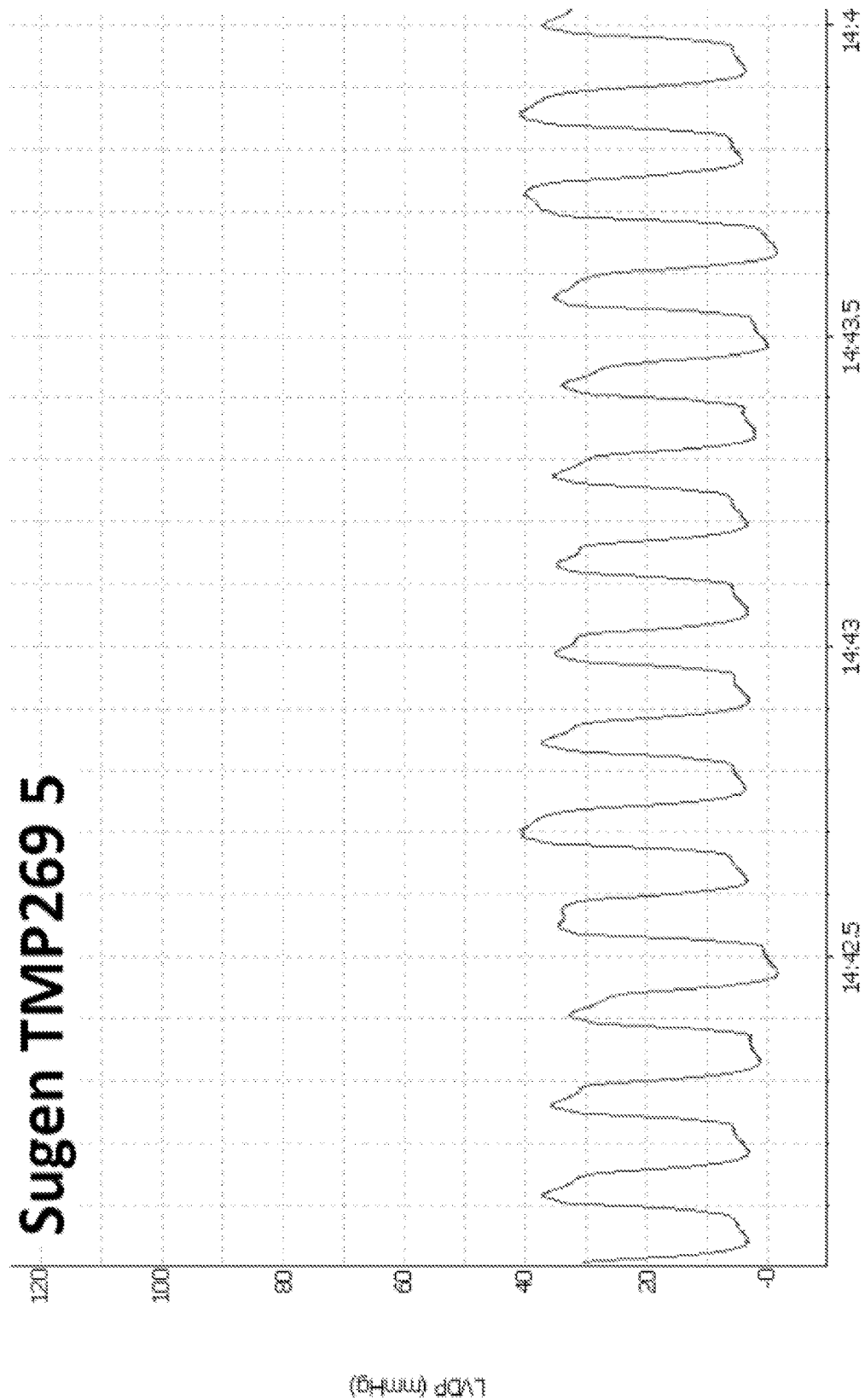
FIG. 36 is a graph showing right ventricular systolic pressure of a rat with pulmonary hypertension treated with TMP269, 5.
Figure 37:
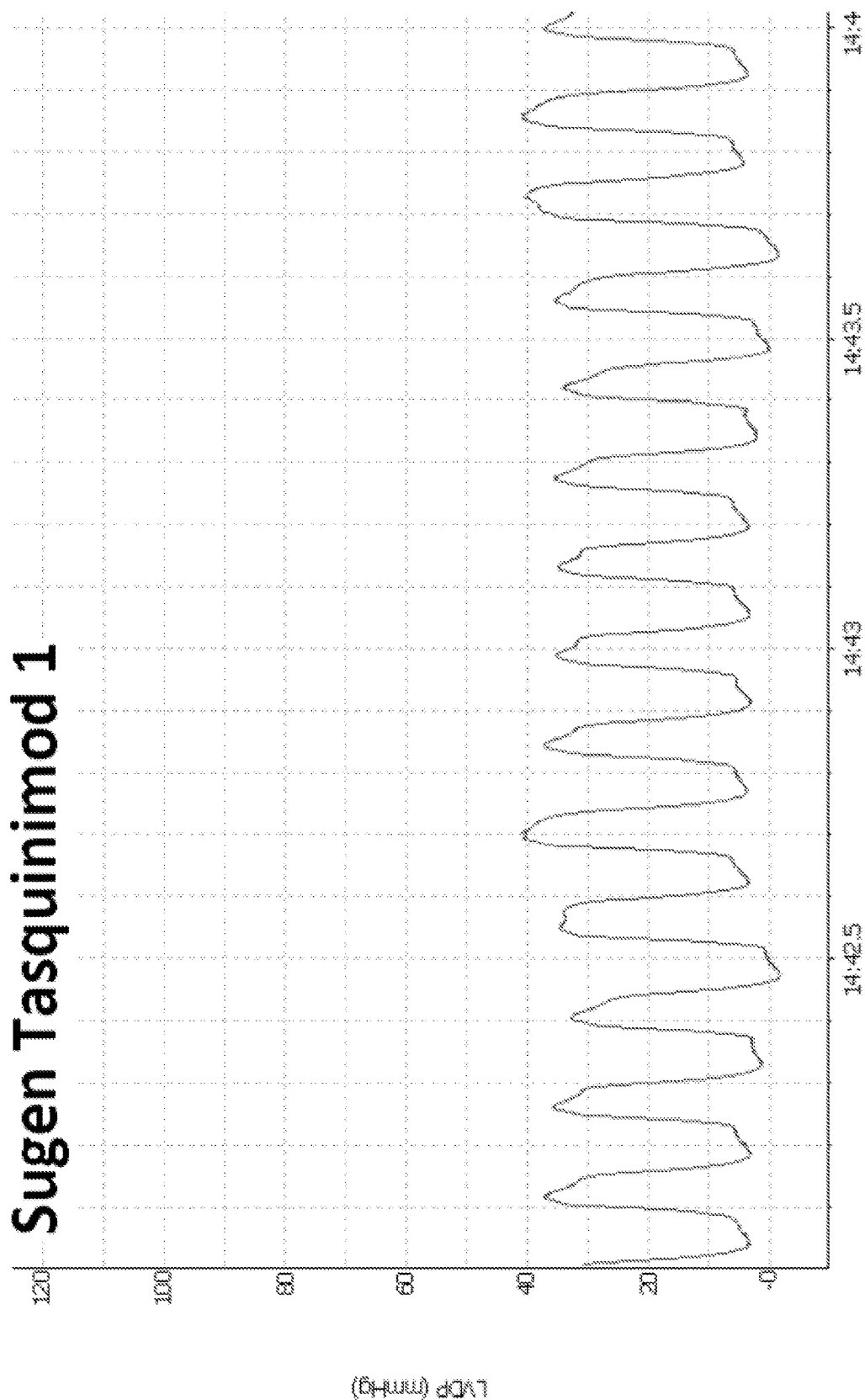
FIG. 37 is a graph showing right ventricular systolic pressure of a rat with pulmonary hypertension treated with Tasquinimod, 1.
Figure 38:
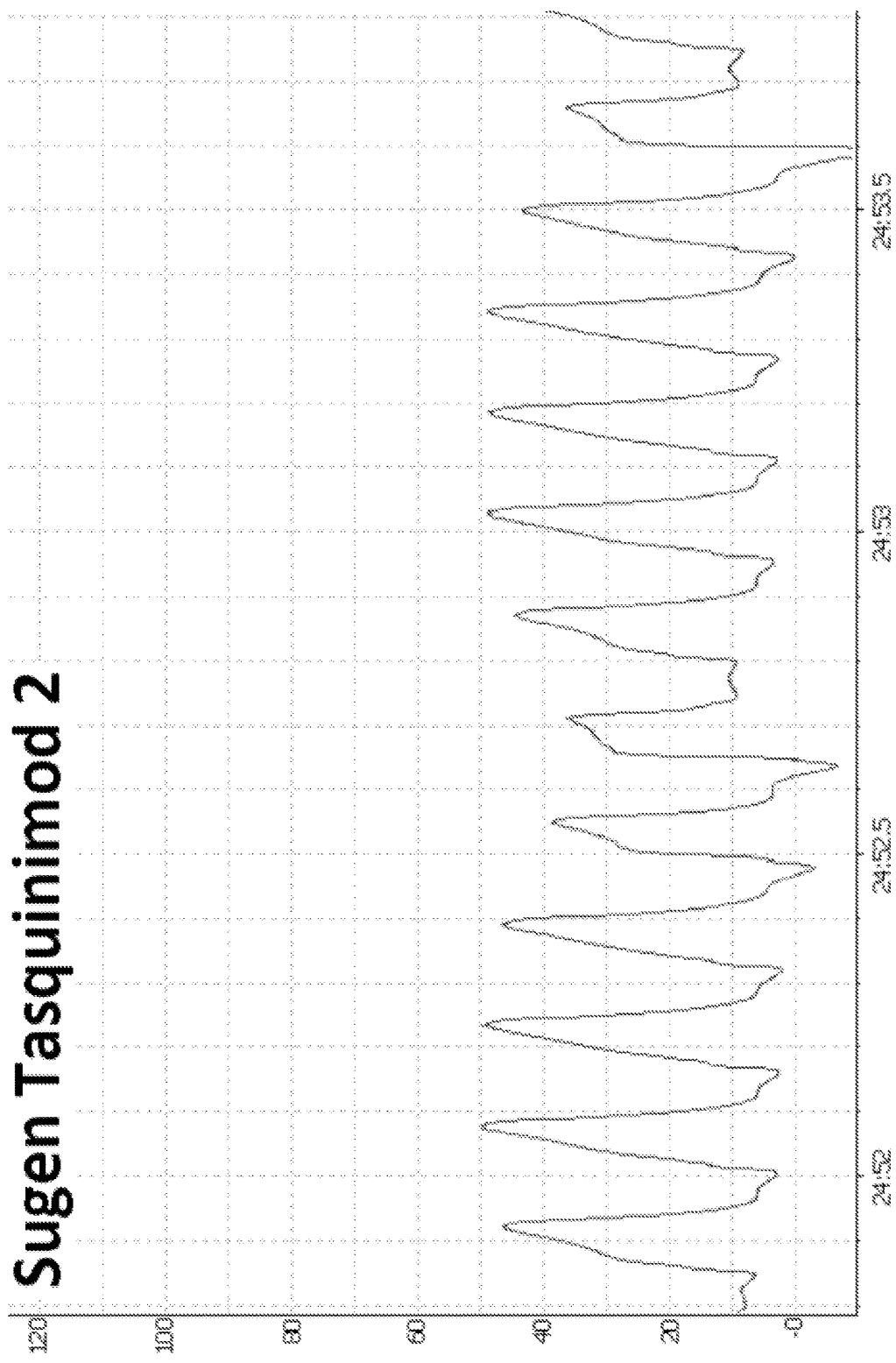
FIG. 38 is a graph showing right ventricular systolic pressure of a rat with pulmonary hypertension treated with Tasquinimod, 2.
Figure 39:
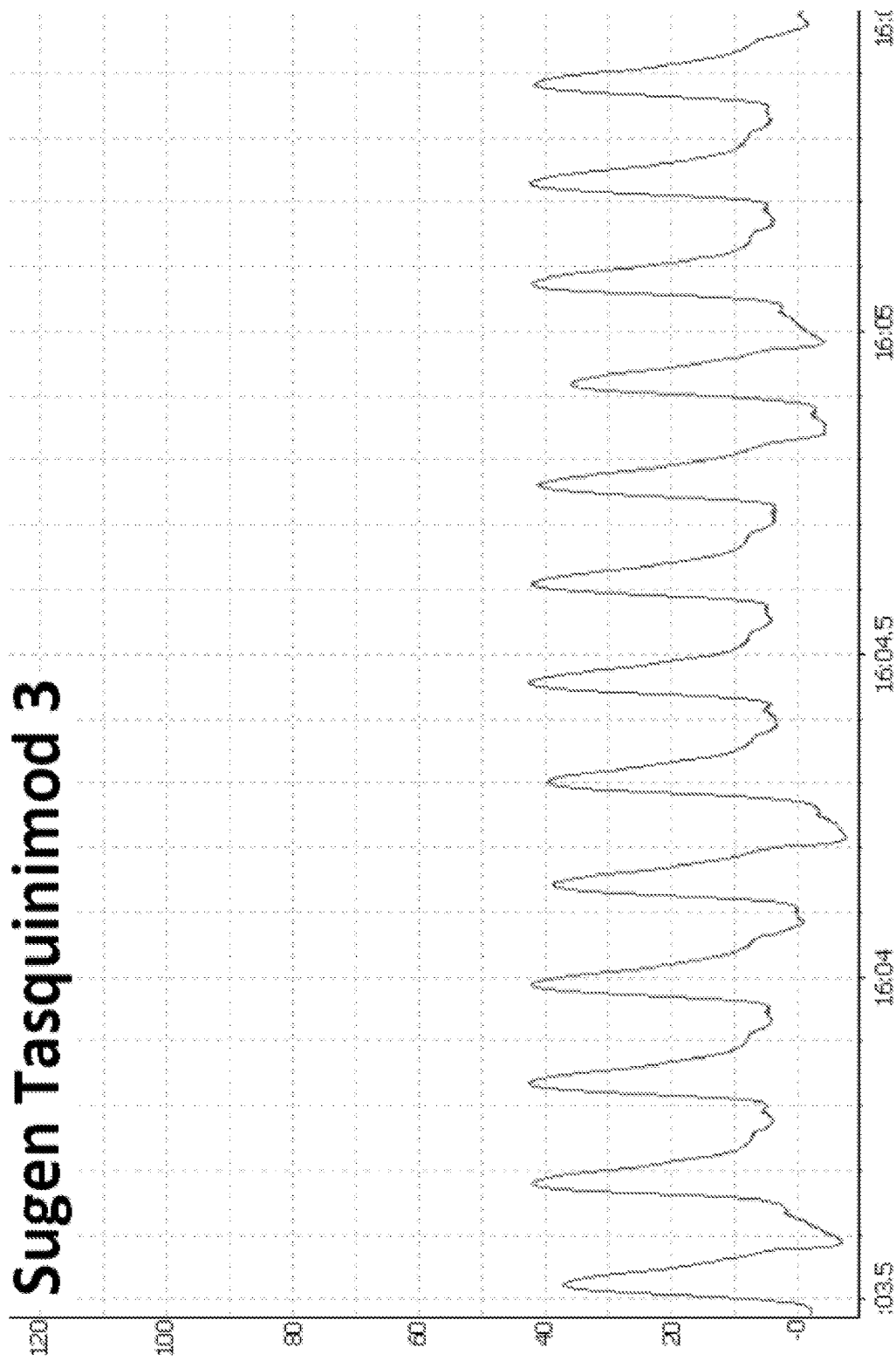
FIG. 39 is a graph showing right ventricular systolic pressure of a rat with pulmonary hypertension treated with Tasquinimod, 3.
Figure 40:
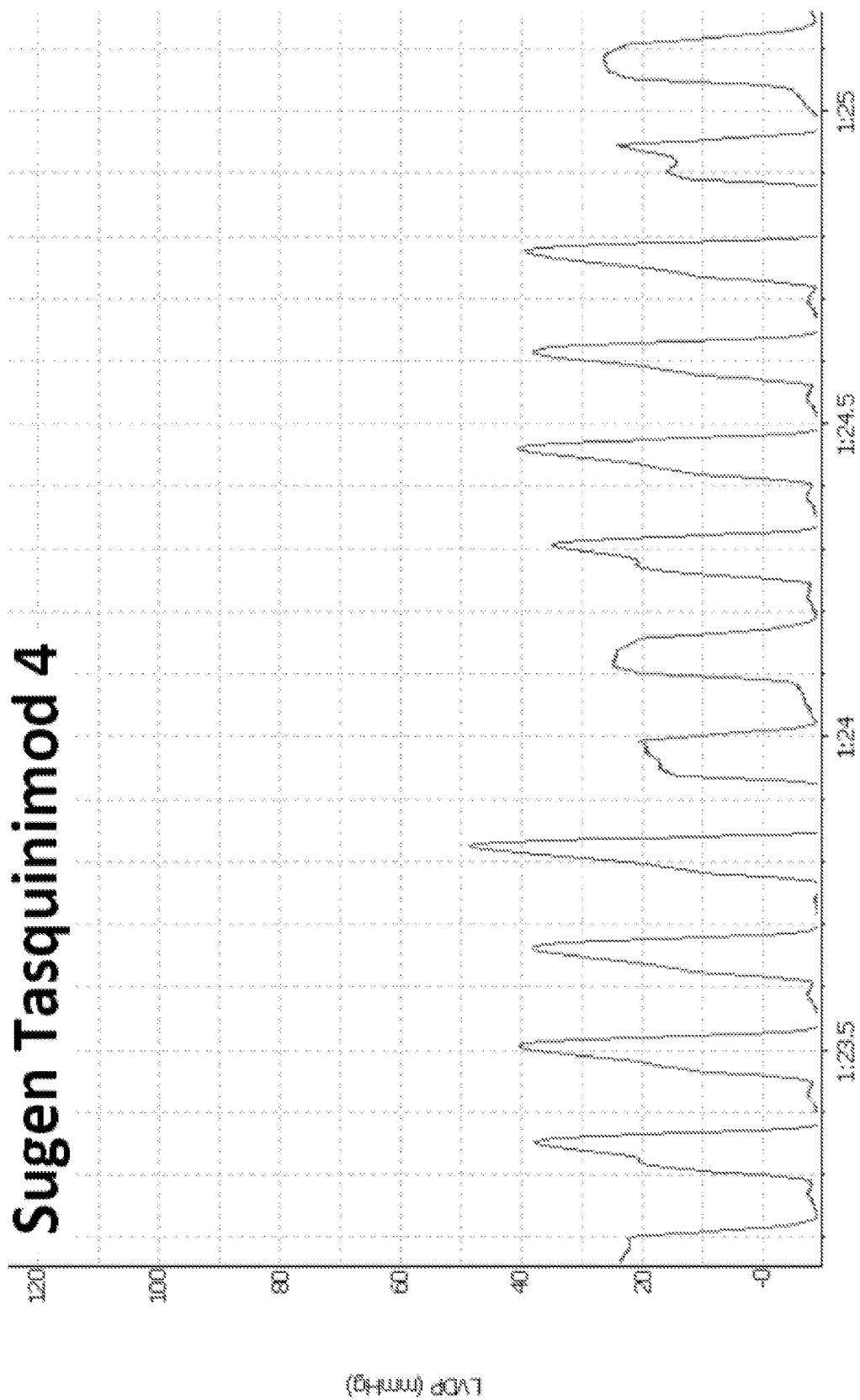
FIG. 40 is a graph showing right ventricular systolic pressure of a rat with pulmonary hypertension treated with Tasquinimod, 4.
Figure 41:
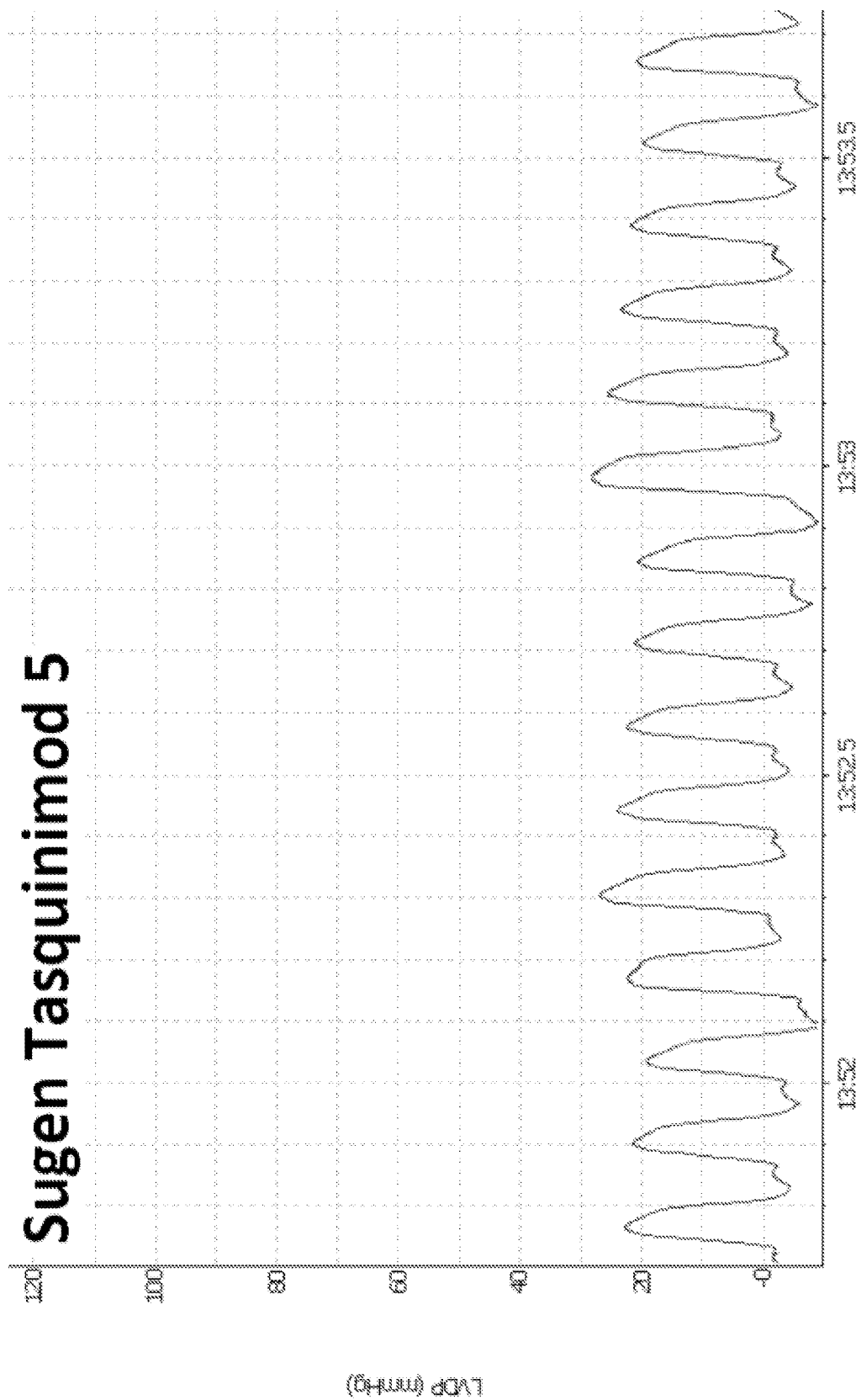
FIG. 41 is a graph showing right ventricular systolic pressure of a rat with pulmonary hypertension treated with Tasquinimod, 5.

Rats that developed experimental pulmonary hypertension, after injection with a VEGFR2 antagonist (SU-5416) and placed in a hypoxia chamber, were also treated with DMSO (control), TMP269 (intraperitoneal injection of 50 mg/kg/day for two weeks), or Tasquinimod (oral gavage of 10 mg/kg/day for two weeks). Both TMP269 and Tasquinimod treated rats has significantly reduced right ventricular systolic pressures, as shown in FIG. 25.

FIGS. 27-41 further demonstrate the right ventricular systolic pressures in rats with experimental pulmonary hypertension treated with TMP269 and Tasquinimod were significantly reduced as compared to rats treated with DMSO.

Figure 42:
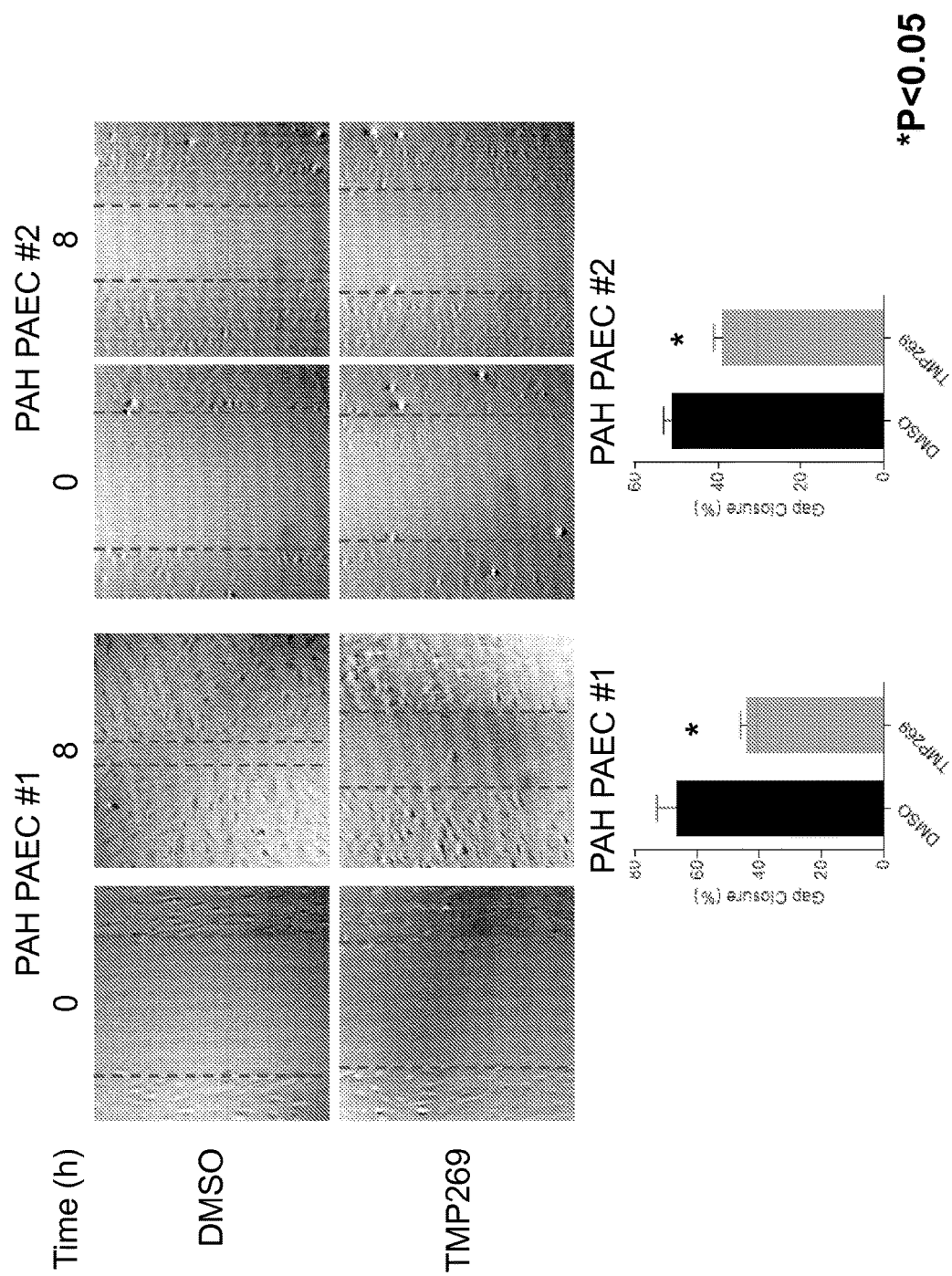
FIG. 42 is a panel of images and graphs showing inhibition of cell migration after treatment of PAECs from PAH patients with TMP269 (1 µM for 24 hr).
Figure 43A:
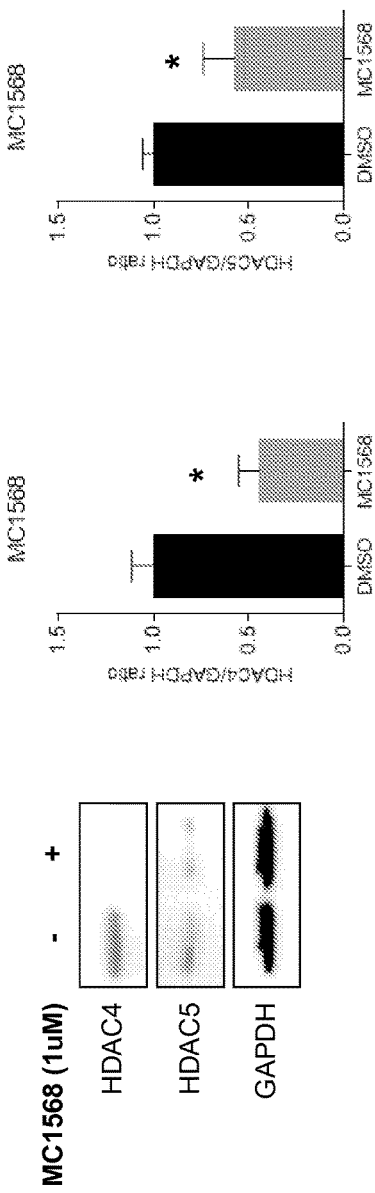
FIG. 43A is a panel of blots and graphs showing degradation of HDAC4 and HDAC5 after treatment of PAECs from a PAH patient with MC1568 (1 µM for 24 hr).
Figure 43B:
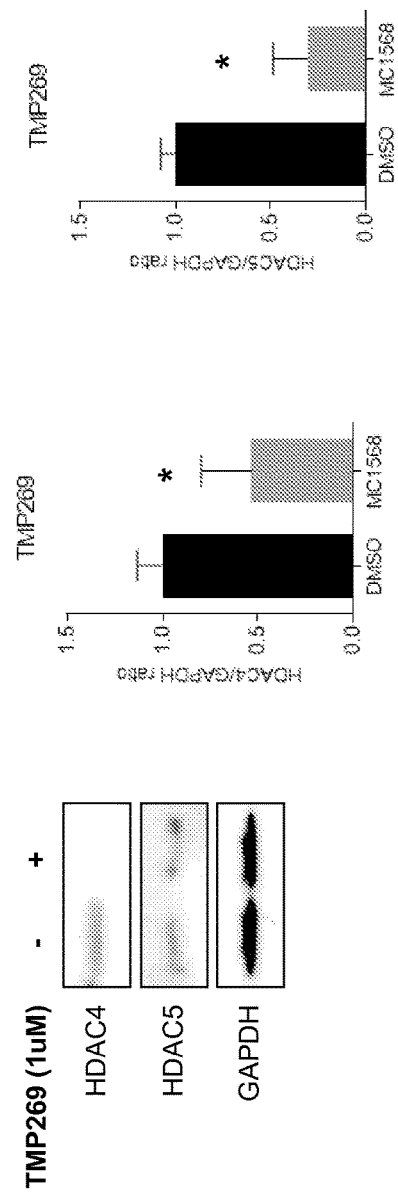
FIG. 43B is a panel of blots and graphs showing degradation of HDAC4 and HDAC5 after treatment of PAECs from a PAH patient with TMP269 (1 µM for 24 hr).

Cell migration was also inhibited after treatment with 1 µM TMP269, see FIG. 42. Moreover, degradation of both HDAC4 and HDAC5 was seen after treatment with MC1568 (FIG. 43A), a derivative of (aryloxopropenyl)pyrrolyl hydroxyamide and a HDAC class II inhibitor, and TMP269 (FIG. 43B).

Figure 44A:
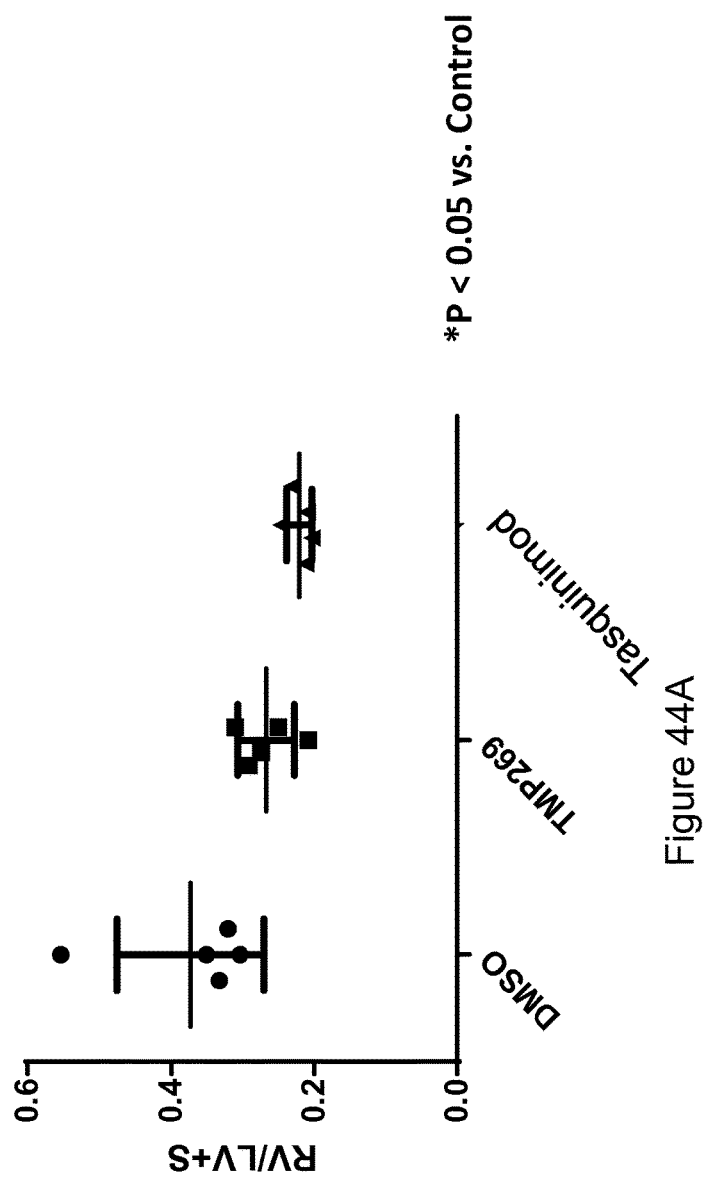
FIG. 44A is a graph showing the decrease of right ventricular hypertrophy as measured by the right ventricle to left ventricle plus septum weight ratios by either TMP269 or Tasquinimod of the experimental rat model of PAH using SU5416/hypoxia.
Figure 44B:
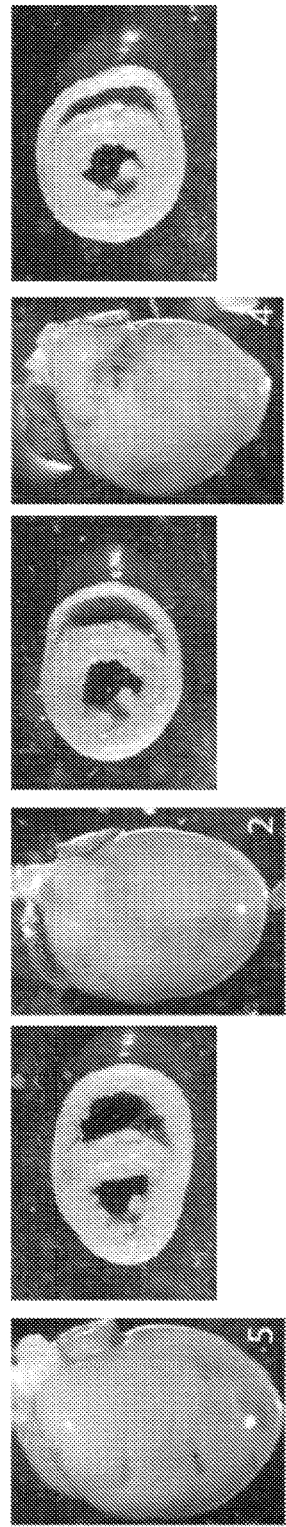
FIG. 44B is a panel of images showing a significant decrease in right ventricular hypertrophy in experimental the rat model of PAH by either TMP269 or Tasquinimod.

Also, right ventricular hypertrophy was decreased in rats that were treated with TMP269 or Tasquinimod, as compared to control, see FIGS. 44A and 44B.

The Materials and Methods used in the performance of the experiments disclosed herein are now described.

Human Samples.

The study was approved by the Cleveland Clinic and the Yale University School of Medicine Institutional Review Boards, and written informed consent was obtained from all participating individuals.

Animal Studies.

Animal experiments performed in this study were approved by the Institutional Animal Care and Use Committee of Yale University.

Cell Culture and Reagents.

PAECs were isolated from normal and PAH explanted donor lungs, as described previously. Additional control PAECs were obtained from Lonza. PAECs from eleven control subjects, seven subjects with IPAH and three subjects with FPAH were studied. In brief, human pulmonary arteries were dissected from the lungs to the distal small arterioles, and PAECs were harvested from the isolated pulmonary arterial tree. PAECs were grown in EBM-2 basal medium supplemented with EGM-2 (Lonza) on fibronectin-coated plates. Cells were passaged at 70-80% confluency, and primary cultures of passages 3 to 7 were used in experiments. All apelin stimulations were done using apelin-13 peptide at 1 µM (Sigma). TSA (Sigma), MC1568 (Selleck Chemicals and DC Chemicals), TMP269 (DC Chemicals), and Tasquinimod (DC Chemicals) were dissolved in DMSO (Sigma) and used at the indicated doses.

Antibodies.

Antibodies to phospho-HDAC4 and phospho-HDAC5 (3443, 3424, Cell Signaling), HDAC4 and HDAC5 (2072, 2082, Cell Signaling), caspase 3 (9662, Cell Signaling), GAPDH (2118s, Cell Signaling) were used for western blotting. Antibodies to vWF (A0082, DAKO), PCNA (M0879, DAKO and 2586, Cell signaling), SMA-Cy3 (C6198, Sigma), were used for immunofluorescence. Alexa 488 (A11008 and A11001, Invitrogen) and Alexa 568 (A11011 and A10037, Invitrogen) conjugated secondary antibodies were used. MEF2 (sc-313X, Santa Cruz) antibody and rabbit IgG control were used for the chromatin immunoprecipitation assays.

siRNAs and Transfection.

SiRNAs against APLN, MEF2A, MEF2C, HDAC4 and HDAC5, as well as non-targeting control siRNAs were purchased from Invitrogen. siRNA was complexed with a lipid transfection reagent (Lipofectamine RNAiMAX, Invitrogen) according to the manufacturer's instructions.

RNA Extraction, RT-PCR and miRNA Profiling.

Total RNA was extracted with an RNA isolation kit, (miRNeasy RNA, Qiagen). Purified RNA was reverse transcribed with a cDNA synthesis kit (iScript cDNA Synthesis Kit, Bio-Rad). RT-PCR was performed with TaqMan probes for both genes and miRNAs (Applied Biosystems). All miRNA data were normalized to the internal control small RNAs RNU19 and HY3 for human samples and U87 for rat samples. For the mRNA samples, ribosomal 18S was used as an internal control. Individual RT-PCRs were performed on a CFX96 (Bio-Rad) according to the manufacturer's instructions.

Chromatin Immunoprecipitation Assay.

PAECs were transfected with control siRNA or APLN siRNAs (Invitrogen) for 48 hours, and native protein-DNA complexes were crosslinked by treatment with 1% formaldehyde for 15 minutes. Simple ChIP Plus Enzymatic Chromatin IP kit (Cell Signaling) was used per the manufacturer's protocol. Briefly, equal aliquots of isolated chromatin were subjected to immunoprecipitation with anti-MEF2 antibody or rabbit IgG control.

Immunohistochemistry of Lung Sections.

Rat lung tissues were fixed and stained as previously described (Nature medicine 19, 74-82 (2013)). Standard methods (Trichrome Stain, Sigma) were used to stain for collagen in cardiac sections.

Immunofluorescence.

For the apelin effect on HDAC4/5 translocation, PAECs plated on glass bottom culture dish (Mat-Tek) were transfected with GFP-tagged HDAC4 and HDAC5 expression vectors for 24 hours. Cells were imaged using a Nikon Eclipse Ti confocal microscopy before and after treatment with apelin 13 (1 µM for 1 h at 37° C.).

Luciferase Assays.

Either control PAECs or PAH PAECs were transfected and lysed in lysis buffer (Promega). Renilla luciferase was used for normalization. Dual Luciferase Reporter System (Promega) was used according to the manufacturer's protocol. All experiments were performed three times in triplicates.

Protein Methods.

Western blotting was performed as previously described (eriosclerosis, thrombosis, and vascular biology 31, 814-820 (2011)). Each western blot is representative of three independent experiments done in triplicate. For the generation of cell lysates, lysis buffer (RIPA, Thermo Scientific) containing a protease and phosphatase inhibitor cocktail (Halt Protease and Phosphatase Inhibitor, Thermo Scientific) was used. Protein contents were measured using a detergent-compatible protein concentration assay (DC™ assay, Bio-Rad).

Proliferation Assays.

PAECs ($5\times10^3$ cells per well) were plated in a 96-well plate and treated with DMSO or MC1568. Cell proliferation was measured by a colorimetric kit for determining cell viability (CellTiter 96 AQueous One Solution Cell Proliferation Assay, Promega) per manufacturer's protocol.

Cell Migration Assays.

PAECs were grown to post-confluence in 24-well plates, and then subjected to injury using a plastic pipette tip. They were then treated with vehicle or MC1568 (1 µM). The cells were allowed to migrate for 8 h, and the gap distance was calculated in at least five randomly selected microscopic fields per each sample.

Pulmonary Hypertension Animal Models.

Male Sprague Dawley rats (200-250 g; Charles River Laboratories) were subcutaneously injected with monocrotaline (Sigma) (60 mg per kg body weight) for the MCT model. For the SUGEN model, SU-5416 (Sigma) was resuspended in DMSO (Sigma) and injected subcutaneously (20 mg per kg body weight). Rats were subsequently exposed to hypoxia (10% $FiO_2$) for 2 weeks. Rats were given intraperitoneal administration of either the vehicle (DMSO), MC1568 (Sellek Chemicals and DC Chemicals) (50 mg per kg body weight), TMP269 (DC Chemicals) (intraperitoneal injection of 50 mg/kg/day for two weeks), or Tasquinimod (DC Chemicals) (oral gavage of 10 mg/kg/day for two weeks) daily as indicated (FIG. 13).

Hemodynamic and Morphometric Analyses.

Right ventricular systolic pressure (RVSP) measurements were performed at the designated time points under isoflurane by inserting a catheter (Millar Instruments) into the right jugular vein as described previously.[21] Lungs were perfused with normal saline and fixed in 4% paraformaldehyde overnight for immunohistochemistry or snap frozen in liquid nitrogen for protein and RNA analyses. Hearts were dissected and weighed for calculation of the right ventricle to the left ventricle plus septum weight ratio. The same full section in the midportion of the left lung parallel to the hilum was used and embedded in the same manner for lung morphometric analyses. Pulmonary artery muscularization was assessed at ×200 magnification after staining for vWF and SMA by calculating the ratio of the number of muscularized peripheral pulmonary arteries to the number of total peripheral pulmonary arteries (with diameters less than 75 µm) in five random fields per lung (with each field at ×200 magnification). The total number of vessels less than 75 µm was expressed as the number of vessels counted per random microscope field (five random fields per lung at ×200 magnification). Pulmonary arteries with proliferating cells were assessed in PCNA stained lung sections. Vessels with one or more PCNA staining cell were considered to be PNCA positive. All measurements were carried out by investigators blinded to the experimental condition.

Statistical Analyses.

All experiments were performed in triplicate (unless otherwise specified) from at least three independent experiments, and data shown are the means±s.e.m. When only two groups were compared, statistical differences were assessed with unpaired two-tailed Student's t test. Otherwise, statistical significance was determined using one-way analysis of variance followed by Bonferroni's multiple comparison test. Relationships between variables were determined by the Pearson correlation coefficient. $P<0.05$ was considered statistically significant.

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for treating pulmonary hypertension in a subject in need thereof comprising administering to the subject a composition comprising tasquinimod or a salt or solvate thereof.

2. The method of claim 1, wherein the administration increases expression of at least one transcriptional target selected from the group consisting of myocyte enhancer factor 2 (MEF2), kruppel like factor 2 (KLF2), connexin 37 (Cx37), connexin 40 (Cx40), and combinations thereof.

3. The method of claim 1, wherein the administration decreases expression of fibroblast growth factor 2 (FGF2).

4. The method of claim 1, wherein the administration decreases proliferation of pulmonary vascular cells.

5. The method of claim 1, wherein the administration decreases ventricular systolic pressure in the subject.

6. The method of claim 1, wherein the administration does not induce a caspase pathway activation in pulmonary vascular cells.

7. The method of claim 1, wherein the administration does not induce myocardial fibrosis.

8. The method of claim 1, wherein the composition inhibits at least one of HDAC4, HDAC5 and combinations thereof.

* * * * *